United States Patent
Kurtzman et al.

(10) Patent No.: US 10,858,442 B2
(45) Date of Patent: Dec. 8, 2020

(54) ANTIBODIES THAT TARGET HUMAN CD47

(71) Applicant: QLSF Biotherapeutics Inc., South San Francisco, CA (US)

(72) Inventors: Aaron Kurtzman, Redwood City, CA (US); Shihao Chen, San Mateo, CA (US)

(73) Assignee: QLSF BIOTHERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 16/852,260

(22) Filed: Apr. 17, 2020

(65) Prior Publication Data

US 2020/0332019 A1    Oct. 22, 2020

Related U.S. Application Data

(60) Provisional application No. 62/835,737, filed on Apr. 18, 2019.

(51) Int. Cl.
*C07K 16/00* (2006.01)
*A61K 39/395* (2006.01)
*C07K 16/28* (2006.01)

(52) U.S. Cl.
CPC ...... *C07K 16/2896* (2013.01); *C07K 2317/21* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01)

(58) Field of Classification Search
None
See application file for complete search history.

(56) References Cited

U.S. PATENT DOCUMENTS

2008/0107654 A1   5/2008   Kikuchi et al.
2017/0081407 A1   3/2017   Grosveld et al.

FOREIGN PATENT DOCUMENTS

| WO | 2015133882 A1 | 9/2015 |
| WO | 2016081423 A1 | 5/2016 |
| WO | 2017049251 A2 | 3/2017 |

OTHER PUBLICATIONS

International Search Report on PCT/US2020/28851, dated Sep. 8, 2020.

*Primary Examiner* — Mark Halvorson
(74) *Attorney, Agent, or Firm* — Lin Sun-Hoffman; Yong Chen; Liu Chen & Hoffman LLP

(57) ABSTRACT

Provided are isolated antibodies that bind to and block CD47, vectors comprising a nucleic acid molecule encoding an amino acid sequence of the binding molecule, and host cells containing the vectors. Methods of making the antibodies, pharmaceutical compositions containing the antibodies, and methods of using such antibodies, antibody fragments and derivatives and polypeptides, such as in treating diseases including cancer, are also provided.

23 Claims, 6 Drawing Sheets

Specification includes a Sequence Listing.

SEQUENCE LISTING

<160> NUMBER OF SEQ ID NOS: 68

<210> SEQ ID NO 1
<211> LENGTH: 113
<212> TYPE: PRT
<213> ORGANISM: Mus musculus

<400> SEQUENCE: 1

```
Asp Ile Val Met Ser Gln Ser Pro Ser Ser Leu Ala Val Ser Val Arg
1               5                   10                  15

Glu Lys Leu Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Ser Tyr Pro Leu Thr Phe Gly Ala Gly Thr Lys Leu Glu Leu
            100                 105                 110

Lys
```

<210> SEQ ID NO 2
<211> LENGTH: 112

```
<212> TYPE: PRT
<213> ORGANISM: Mus musculus

<400> SEQUENCE: 2

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Lys Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Arg Arg Tyr Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Arg Leu Glu Ile Lys
            100                 105                 110

<210> SEQ ID NO 3
<211> LENGTH: 112
<212> TYPE: PRT
<213> ORGANISM: Mus musculus

<400> SEQUENCE: 3

Asp Val Leu Met Thr Gln Thr Pro Leu Ser Leu Pro Val Ser Leu Gly
1               5                   10                  15

Asp Gln Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 4
<211> LENGTH: 124
<212> TYPE: PRT
<213> ORGANISM: Mus musculus

<400> SEQUENCE: 4

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Asp Lys Gly Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
```

85                  90                  95

Val Arg Lys Gly Ile Ile Tyr Asn Tyr Gly Ser Ser Asp Val Leu Ala
                100                 105                 110

Tyr Trp Gly Gln Gly Thr Leu Val Thr Val Ser Ala
                115                 120

<210> SEQ ID NO 5
<211> LENGTH: 117
<212> TYPE: PRT
<213> ORGANISM: Mus musculus

<400> SEQUENCE: 5

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ser His Gly Lys Ser Leu Glu Trp Ile
                35                  40                  45

Gly Asp Leu Asn Pro Asp Asn Gly Asp Thr Asn Tyr Asn Gln Lys Phe
                50                  55                  60

Val Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Gly Lys Gly Gly Phe Asp Tyr Trp Gly Gln Gly Thr Thr
                100                 105                 110

Leu Thr Val Ser Ser
        115

<210> SEQ ID NO 6
<211> LENGTH: 117
<212> TYPE: PRT
<213> ORGANISM: Mus musculus

<400> SEQUENCE: 6

Gln Val Gln Leu Gln Gln Ser Gly Thr Glu Leu Val Arg Pro Gly Thr
1               5                   10                  15

Ser Val Lys Ile Ser Cys Lys Ala Ser Gly Tyr Ser Leu Ile Asn Tyr
                20                  25                  30

Trp Val Gly Trp Val Lys Gln Arg Pro Gly His Gly Leu Glu Trp Ile
                35                  40                  45

Gly Asp Val Tyr Pro Gly Gly Asn Tyr Thr Asn Asn Asn Glu Lys Leu
                50                  55                  60

Lys Gly Lys Ala Thr Leu Thr Ala Asp Thr Ser Ala Ser Thr Ala Tyr
65                  70                  75                  80

Leu Gln Leu Ser Ser Leu Thr Ser Glu Asp Ser Ala Val Tyr Phe Cys
                85                  90                  95

Ala Arg Lys Gly Arg Gly Gly Met Asp Tyr Trp Gly Gln Gly Thr Ser
                100                 105                 110

Val Thr Val Ser Ser
        115

<210> SEQ ID NO 7
<211> LENGTH: 17
<212> TYPE: PRT
<213> ORGANISM: Mus musculus

<400> SEQUENCE: 7

Lys Ser Ser Gln Ser Leu Leu Tyr Ser Asn Gln Lys Asn Tyr Leu
1               5                   10                  15

Ala

<210> SEQ ID NO 8
<211> LENGTH: 16
<212> TYPE: PRT
<213> ORGANISM: Mus musculus

<400> SEQUENCE: 8

Arg Ser Ser Gln Ser Leu Glu Lys Ser Asn Gly Asn Thr Tyr Leu Asn
1               5                   10                  15

<210> SEQ ID NO 9
<211> LENGTH: 16
<212> TYPE: PRT
<213> ORGANISM: Mus musculus

<400> SEQUENCE: 9

Arg Ser Thr Gln Ser Ile Val His Ser Asn Gly Lys Thr Tyr Leu Glu
1               5                   10                  15

<210> SEQ ID NO 10
<211> LENGTH: 7
<212> TYPE: PRT
<213> ORGANISM: Mus musculus

<400> SEQUENCE: 10

Trp Ala Ser Thr Arg Glu Ser
1               5

<210> SEQ ID NO 11
<211> LENGTH: 7
<212> TYPE: PRT
<213> ORGANISM: Mus musculus

<400> SEQUENCE: 11

Arg Val Ser Arg Arg Tyr Ser
1               5

<210> SEQ ID NO 12
<211> LENGTH: 7
<212> TYPE: PRT
<213> ORGANISM: Mus musculus

<400> SEQUENCE: 12

Arg Val Ser Asn Arg Phe Ser
1               5

<210> SEQ ID NO 13
<211> LENGTH: 9
<212> TYPE: PRT
<213> ORGANISM: Mus musculus

<400> SEQUENCE: 13

His Gln Tyr Tyr Ser Tyr Pro Leu Thr
1               5

<210> SEQ ID NO 14
<211> LENGTH: 9
<212> TYPE: PRT
<213> ORGANISM: Mus musculus

<400> SEQUENCE: 14

Leu Gln Val Thr His Val Pro Tyr Thr
1               5

<210> SEQ ID NO 15
<211> LENGTH: 9
<212> TYPE: PRT
<213> ORGANISM: Mus musculus

<400> SEQUENCE: 15

Phe Gln Gly Ser His Val Pro Phe Thr
1               5

<210> SEQ ID NO 16
<211> LENGTH: 5
<212> TYPE: PRT
<213> ORGANISM: Mus musculus

<400> SEQUENCE: 16

Asp Tyr Tyr Ile Asn
1               5

<210> SEQ ID NO 17
<211> LENGTH: 5
<212> TYPE: PRT
<213> ORGANISM: Mus musculus

<400> SEQUENCE: 17

Gly Tyr Tyr Met Asn
1               5

<210> SEQ ID NO 18
<211> LENGTH: 5
<212> TYPE: PRT
<213> ORGANISM: Mus musculus

<400> SEQUENCE: 18

Asn Tyr Trp Val Gly
1               5

<210> SEQ ID NO 19
<211> LENGTH: 17
<212> TYPE: PRT
<213> ORGANISM: Mus musculus

<400> SEQUENCE: 19

Trp Ile Tyr Pro Gly Ser Gly Asn Thr Lys Tyr Asn Glu Lys Phe Lys
1               5                   10                  15

Asp

<210> SEQ ID NO 20
<211> LENGTH: 17
<212> TYPE: PRT
<213> ORGANISM: Mus musculus

<400> SEQUENCE: 20

Asp Leu Asn Pro Asp Asn Gly Asp Thr Asn Tyr Asn Gln Lys Phe Val
1               5                   10                  15

Gly

<210> SEQ ID NO 21
<211> LENGTH: 17
<212> TYPE: PRT
<213> ORGANISM: Mus musculus

<400> SEQUENCE: 21

Asp Val Tyr Pro Gly Gly Asn Tyr Thr Asn Asn Glu Lys Leu Lys
1               5                   10                  15

Gly

<210> SEQ ID NO 22
<211> LENGTH: 15
<212> TYPE: PRT
<213> ORGANISM: Mus musculus

<400> SEQUENCE: 22

Lys Gly Ile Ile Tyr Asn Tyr Gly Ser Ser Asp Val Leu Ala Tyr
1               5                   10                  15

<210> SEQ ID NO 23
<211> LENGTH: 8
<212> TYPE: PRT
<213> ORGANISM: Mus musculus

<400> SEQUENCE: 23

Gly Gly Lys Gly Gly Phe Asp Tyr
1               5

<210> SEQ ID NO 24
<211> LENGTH: 8
<212> TYPE: PRT
<213> ORGANISM: Mus musculus

<400> SEQUENCE: 24

Lys Gly Arg Gly Gly Met Asp Tyr
1               5

<210> SEQ ID NO 25
<211> LENGTH: 113
<212> TYPE: PRT
<213> ORGANISM: Artificial Sequence
<220> FEATURE:
<223> OTHER INFORMATION: Humanized light chain variable domain

<400> SEQUENCE: 25

Asp Ile Val Met Thr Gln Ser Pro Asp Ser Leu Ala Val Ser Leu Gly
1               5                   10                  15

Glu Arg Leu Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Leu
            100                 105                 110

Lys

<210> SEQ ID NO 26
<211> LENGTH: 113
<212> TYPE: PRT
<213> ORGANISM: Artificial Sequence
<220> FEATURE:
<223> OTHER INFORMATION: Humanized light chain variable domain

<400> SEQUENCE: 26

Asp Ile Val Met Thr Gln Ser Pro Asp Ser Leu Ala Val Ser Leu Gly
1               5                   10                  15

Glu Arg Leu Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Leu
            100                 105                 110

Lys

<210> SEQ ID NO 27
<211> LENGTH: 113
<212> TYPE: PRT
<213> ORGANISM: Artificial Sequence
<220> FEATURE:
<223> OTHER INFORMATION: Humanized light chain variable domain

<400> SEQUENCE: 27

Asp Ile Val Met Thr Gln Ser Pro Ser Ser Leu Ala Val Ser Leu Arg
1               5                   10                  15

Glu Arg Leu Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Leu
            100                 105                 110

Lys

<210> SEQ ID NO 28
<211> LENGTH: 112
<212> TYPE: PRT
<213> ORGANISM: Artificial Sequence
<220> FEATURE:
<223> OTHER INFORMATION: Humanized light chain variable domain

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Lys Ser
            20                  25                  30

Asn Gly Asn Thr Tyr Leu Asn Trp Phe Gln Gln Arg Pro Gly Gln Ser
        35                  40                  45

Pro Gln Leu Leu Ile Tyr Arg Val Ser Arg Arg Tyr Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Arg Leu Glu Ile Lys
             100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Humanized light chain variable domain

<400> SEQUENCE: 29

Asp Ala Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Glu Lys Ser
             20                  25                  30

Asn Gly Asn Thr Tyr Leu Asn Trp Tyr Leu Gln Arg Pro Gly Gln Ser
         35                  40                  45

Pro Gln Leu Leu Ile Tyr Arg Val Ser Arg Arg Tyr Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Arg Leu Glu Ile Lys
             100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Humanized light chain variable domain

<400> SEQUENCE: 30

Asp Ala Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Glu Lys Ser
             20                  25                  30

Asn Gly Asn Thr Tyr Leu Asn Trp Tyr Leu Gln Arg Pro Gly Gln Ser
         35                  40                  45

Pro Gln Leu Leu Ile Tyr Arg Val Ser Arg Arg Tyr Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Arg Leu Glu Ile Lys
             100                 105                 110

<210> SEQ ID NO 31
<211> LENGTH: 112
<212> TYPE: PRT

<213> ORGANISM: Artificial Sequence
<220> FEATURE:
<223> OTHER INFORMATION: Humanized light chain variable domain

<400> SEQUENCE: 31

Asp Ala Val Met Thr Gln Ser Pro Leu Ser Leu Pro Val Thr Leu Gly
1               5                   10                  15

Asp Pro Ala Ser Ile Ser Cys Arg Ser Ser Gln Ser Leu Glu Lys Ser
            20                  25                  30

Asn Gly Asn Thr Tyr Leu Asn Trp Tyr Leu Gln Arg Pro Gly Gln Ser
        35                  40                  45

Pro Gln Leu Leu Ile Tyr Arg Val Ser Arg Tyr Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Arg Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Humanized light chain variable domain

<400> SEQUENCE: 32

Asp Val Val Met Thr Gln Thr Pro Leu Ser Leu Ser Val Thr Pro Gly
1               5                   10                  15

Gln Pro Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Humanized light chain variable domain

<400> SEQUENCE: 33

Asp Val Leu Met Thr Gln Thr Pro Leu Ser Leu Ser Val Thr Pro Gly
1               5                   10                  15

Gln Pro Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

-continued

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Humanized light chain variable domain

<400> SEQUENCE: 34

Asp Val Leu Met Thr Gln Thr Pro Leu Ser Leu Ser Val Thr Pro Gly
1               5                   10                  15

Asp Pro Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 35
<211> LENGTH: 124
<212> TYPE: PRT
<213> ORGANISM: Artificial Sequence
<220> FEATURE:
<223> OTHER INFORMATION: Humanized heavy chain variable domain

<400> SEQUENCE: 35

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asp Tyr
            20                  25                  30

Tyr Ile Asn Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Asp Arg Val Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Val Arg Lys Gly Ile Ile Tyr Asn Tyr Gly Ser Ser Asp Val Leu Ala
            100                 105                 110

Tyr Trp Gly Gln Gly Thr Leu Val Thr Val Ser Ser
        115                 120

<210> SEQ ID NO 36
<211> LENGTH: 124
<212> TYPE: PRT

<213> ORGANISM: Artificial Sequence
<220> FEATURE:
<223> OTHER INFORMATION: Humanized heavy chain variable domain

<400> SEQUENCE: 36

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Val Lys Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Asp Arg Val Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Phe Cys
            85                  90                  95

Val Arg Lys Gly Ile Ile Tyr Asn Tyr Gly Ser Ser Asp Val Leu Ala
            100                 105                 110

Tyr Trp Gly Gln Gly Thr Leu Val Thr Val Ser Ser
        115                 120

<210> SEQ ID NO 37
<211> LENGTH: 124
<212> TYPE: PRT
<213> ORGANISM: Artificial Sequence
<220> FEATURE:
<223> OTHER INFORMATION: Humanized heavy chain variable domain

<400> SEQUENCE: 37

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Asp Arg Gly Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Phe Cys
            85                  90                  95

Val Arg Lys Gly Ile Ile Tyr Asn Tyr Gly Ser Ser Asp Val Leu Ala
            100                 105                 110

Tyr Trp Gly Gln Gly Thr Leu Val Thr Val Ser Ser
        115                 120

<210> SEQ ID NO 38
<211> LENGTH: 124
<212> TYPE: PRT
<213> ORGANISM: Artificial Sequence
<220> FEATURE:
<223> OTHER INFORMATION: Humanized heavy chain variable domain

<400> SEQUENCE: 38

Gln Ile Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Ile Asp Tyr
            20                  25                  30

-continued

Tyr Ile Asn Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
    50                  55                  60

Lys Asp Arg Gly Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Val Arg Lys Gly Ile Ile Tyr Asn Tyr Gly Ser Ser Asp Val Leu Ala
                100                 105                 110

Tyr Trp Gly Gln Gly Thr Leu Val Thr Val Ser Ser
            115                 120

<210> SEQ ID NO 39
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 39

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Val Arg Gln Ala Pro Gly Gln Ser Leu Glu Trp Ile
            35                  40                  45

Gly Asp Leu Asn Pro Asp Asn Gly Asp Thr Asn Tyr Asn Gln Lys Phe
    50                  55                  60

Val Gly Arg Val Thr Met Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Gly Lys Gly Gly Phe Asp Tyr Trp Gly Gln Gly Thr Thr
                100                 105                 110

Leu Thr Val Ser Ser
            115

<210> SEQ ID NO 40
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 40

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ala Pro Gly Gln Ser Leu Glu Trp Ile
            35                  40                  45

Gly Asp Leu Asn Pro Asp Asn Gly Asp Thr Asn Tyr Asn Gln Lys Phe
    50                  55                  60

Val Gly Arg Val Thr Met Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys

```
                    85                  90                  95
Ala Arg Gly Gly Lys Gly Gly Phe Asp Tyr Trp Gly Gln Gly Thr Thr
                100                 105                 110

Leu Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 41

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ala Pro Gly Lys Ser Leu Glu Trp Ile
            35                  40                  45

Gly Asp Leu Asn Pro Asp Asn Gly Asp Thr Asn Tyr Asn Gln Lys Phe
    50                  55                  60

Val Gly Arg Ala Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Gly Lys Gly Gly Phe Asp Tyr Trp Gly Gln Gly Thr Thr
                100                 105                 110

Leu Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 42

Glu Val Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ser His Gly Lys Ser Leu Glu Trp Ile
            35                  40                  45

Gly Asp Leu Asn Pro Asp Asn Gly Asp Thr Asn Tyr Asn Gln Lys Phe
    50                  55                  60

Val Gly Arg Ala Thr Leu Thr Val Asp Lys Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Gly Lys Gly Gly Phe Asp Tyr Trp Gly Gln Gly Thr Thr
                100                 105                 110

Leu Thr Val Ser Ser
        115

<210> SEQ ID NO 43
<211> LENGTH: 117
```

```
<212> TYPE: PRT
<213> ORGANISM: Artificial Sequence
<220> FEATURE:
<223> OTHER INFORMATION: Humanized heavy chain variable domain

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Ile Asn Tyr
            20                  25                  30

Trp Val Gly Trp Val Arg Gln Ala Pro Gly Gln Gly Leu Glu Trp Met
        35                  40                  45

Gly Asp Val Tyr Pro Gly Gly Asn Tyr Thr Asn Asn Glu Lys Leu
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Lys Gly Arg Gly Met Asp Tyr Trp Gly Gln Gly Thr Thr
            100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 44

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Leu Ile Asn Tyr
            20                  25                  30

Trp Val Gly Trp Val Arg Gln Ala Pro Gly Gln Gly Leu Glu Trp Ile
        35                  40                  45

Gly Asp Val Tyr Pro Gly Gly Asn Tyr Thr Asn Asn Glu Lys Leu
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Lys Gly Arg Gly Met Asp Tyr Trp Gly Gln Gly Thr Thr
            100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 45

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Leu Ile Asn Tyr
```

```
                    20                  25                  30
Trp Val Gly Trp Val Arg Gln Ala Pro Gly His Gly Leu Glu Trp Ile
            35                  40                  45
Gly Asp Val Tyr Pro Gly Gly Asn Tyr Thr Asn Asn Asn Glu Lys Leu
        50                  55                  60
Lys Gly Arg Ala Thr Leu Thr Ala Asp Thr Ser Ser Thr Ala Tyr
65                  70                  75                  80
Leu Glu Leu Ser Ser Leu Arg Ser Glu Asp Thr Ala Val Tyr Phe Cys
                85                  90                  95
Ala Arg Lys Gly Arg Gly Gly Met Asp Tyr Trp Gly Gln Gly Thr Thr
            100                 105                 110
Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: Humanized heavy chain variable domain

<400> SEQUENCE: 46

Gln Val Gln Leu Gln Gln Ser Gly Ala Glu Val Lys Lys Pro Gly Ala
1               5                   10                  15
Ser Val Lys Val Ser Cys Lys Ala Ser Gly Tyr Ser Leu Ile Asn Tyr
                20                  25                  30
Trp Val Gly Trp Val Arg Gln Ala Pro Gly His Gly Leu Glu Trp Ile
            35                  40                  45
Gly Asp Val Tyr Pro Gly Gly Asn Tyr Thr Asn Asn Asn Glu Lys Leu
        50                  55                  60
Lys Gly Arg Ala Thr Leu Thr Ala Asp Thr Ser Ser Thr Ala Tyr
65                  70                  75                  80
Leu Glu Leu Ser Ser Leu Arg Ser Glu Asp Thr Ala Val Tyr Phe Cys
                85                  90                  95
Ala Arg Lys Gly Arg Gly Gly Met Asp Tyr Trp Gly Gln Gly Thr Thr
            100                 105                 110
Val Thr Val Ser Ser
        115

<210> SEQ ID NO 47
<211> LENGTH: 220
<212> TYPE: PRT
<213> ORGANISM: Artificial Sequence
<220> FEATURE:
<223> OTHER INFORMATION: Humanized light chains

<400> SEQUENCE: 47

Asp Ile Val Met Thr Gln Ser Pro Asp Ser Leu Ala Val Ser Leu Gly
1               5                   10                  15
Glu Arg Leu Thr Ile Asn Cys Lys Ser Ser Gln Ser Leu Leu Tyr Ser
                20                  25                  30
Ser Asn Gln Lys Asn Tyr Leu Ala Trp Tyr Gln Gln Lys Pro Gly Gln
            35                  40                  45
Pro Pro Lys Leu Leu Ile Tyr Trp Ala Ser Thr Arg Glu Ser Gly Val
        50                  55                  60
Pro Asp Arg Phe Ser Gly Ser Gly Ser Gly Thr Asp Phe Thr Leu Thr
65                  70                  75                  80
```

```
Ile Ser Ser Val Gln Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 48
<211> LENGTH: 220
<212> TYPE: PRT
<213> ORGANISM: Artificial Sequence
<220> FEATURE:
<223> OTHER INFORMATION: Humanized light chains

<400> SEQUENCE: 48

Asp Ile Val Met Thr Gln Ser Pro Asp Ser Leu Ala Val Ser Leu Gly
1               5                   10                  15

Glu Arg Leu Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220
```

```
<210> SEQ ID NO 49
<211> LENGTH: 220
<212> TYPE: PRT
<213> ORGANISM: Artificial Sequence
<220> FEATURE:
<223> OTHER INFORMATION: Humanized light chains

<400> SEQUENCE: 49

Asp Ile Val Met Thr Gln Ser Pro Ser Ser Leu Ala Val Ser Leu Arg
1               5                   10                  15

Glu Arg Leu Thr Ile Asn Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Ala Glu Asp Val Ala Val Tyr Tyr Cys His Gln
                85                  90                  95

Tyr Tyr Ser Tyr Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 50
<211> LENGTH: 219
<212> TYPE: PRT
<213> ORGANISM: Artificial Sequence
<220> FEATURE:
<223> OTHER INFORMATION: Humanized light chains

<400> SEQUENCE: 50

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Lys Ser
            20                  25                  30

Asn Gly Asn Thr Tyr Leu Asn Trp Phe Gln Gln Arg Pro Gly Gln Ser
        35                  40                  45

Pro Gln Leu Leu Ile Tyr Arg Val Ser Arg Arg Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95
```

```
Thr His Val Pro Tyr Thr Phe Gly Gln Gly Thr Arg Leu Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 51
<211> LENGTH: 219
<212> TYPE: PRT
<213> ORGANISM: Artificial Sequence
<220> FEATURE:
<223> OTHER INFORMATION: Humanized light chains

<400> SEQUENCE: 51

Asp Ala Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Lys Ser
            20                  25                  30

Asn Gly Asn Thr Tyr Leu Asn Trp Tyr Leu Gln Arg Pro Gly Gln Ser
        35                  40                  45

Pro Gln Leu Leu Ile Tyr Arg Val Ser Arg Arg Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Arg Leu Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 52
```

```
<211> LENGTH: 219
<212> TYPE: PRT
<213> ORGANISM: Artificial Sequence
<220> FEATURE:
<223> OTHER INFORMATION: Humanized light chains

<400> SEQUENCE: 52

Asp Ala Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Lys Ser
            20                  25                  30

Asn Gly Asn Thr Tyr Leu Asn Trp Tyr Leu Gln Arg Pro Gly Gln Ser
        35                  40                  45

Pro Gln Leu Leu Ile Tyr Arg Val Ser Arg Arg Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 53
<211> LENGTH: 219
<212> TYPE: PRT
<213> ORGANISM: Artificial Sequence
<220> FEATURE:
<223> OTHER INFORMATION: Humanized light chains

<400> SEQUENCE: 53

Asp Ala Val Met Thr Gln Ser Pro Leu Ser Leu Pro Val Thr Leu Gly
1               5                   10                  15

Asp Pro Ala Ser Ile Ser Cys Arg Ser Ser Gln Ser Leu Glu Lys Ser
            20                  25                  30

Asn Gly Asn Thr Tyr Leu Asn Trp Tyr Leu Gln Arg Pro Gly Gln Ser
        35                  40                  45

Pro Gln Leu Leu Ile Tyr Arg Val Ser Arg Arg Tyr Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Arg Leu Glu Ile Lys
```

```
            100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215

<210> SEQ ID NO 54
<211> LENGTH: 219
<212> TYPE: PRT
<213> ORGANISM: Artificial Sequence
<220> FEATURE:
<223> OTHER INFORMATION: Humanized light chains

<400> SEQUENCE: 54

Asp Val Val Met Thr Gln Thr Pro Leu Ser Leu Ser Val Thr Pro Gly
1               5                   10                  15

Gln Pro Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215

<210> SEQ ID NO 55
<211> LENGTH: 219
<212> TYPE: PRT
```

<213> ORGANISM: Artificial Sequence
<220> FEATURE:
<223> OTHER INFORMATION: Humanized light chains

<400> SEQUENCE: 55

Asp Val Leu Met Thr Gln Thr Pro Leu Ser Leu Ser Val Thr Pro Gly
1               5                   10                  15

Gln Pro Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 56
<211> LENGTH: 219
<212> TYPE: PRT
<213> ORGANISM: Artificial Sequence
<220> FEATURE:
<223> OTHER INFORMATION: Humanized light chains

<400> SEQUENCE: 56

Asp Val Leu Met Thr Gln Thr Pro Leu Ser Leu Ser Val Thr Pro Gly
1               5                   10                  15

Asp Pro Ala Ser Ile Ser Cys Arg Ser Thr Gln Ser Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

```
Arg Thr Val Ala Ala Pro Ser Val Phe Ile Phe Pro Ser Asp Glu
            115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
    195                 200                 205
Pro Val Thr Lys Ser Phe Asn Arg Gly Glu Cys
    210                 215

<210> SEQ ID NO 57
<211> LENGTH: 450
<212> TYPE: PRT
<213> ORGANISM: Artificial Sequence
<220> FEATURE:
<223> OTHER INFORMATION: Humanized heavy chains

<400> SEQUENCE: 57

Gln Ile Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ile Asp Tyr
            20                  25                  30
Tyr Ile Asn Trp Val Arg Gln Ala Pro Gly Gln Gly Leu Glu Trp Met
        35                  40                  45
Gly Trp Ile Tyr Pro Gly Ser Gly Asn Thr Lys Tyr Asn Glu Lys Phe
    50                  55                  60
Lys Asp Arg Val Thr Leu Thr Val Asp Thr Ser Ser Ser Thr Ala Tyr
65                  70                  75                  80
Met Glu Leu Ser Ser Leu Arg Ser Glu Asp Thr Ala Val Tyr Tyr Cys
                85                  90                  95
Val Arg Lys Gly Ile Ile Tyr Asn Tyr Gly Ser Ser Asp Val Leu Ala
            100                 105                 110
Tyr Trp Gly Gln Gly Thr Leu Val Thr Val Ser Ser Ala Ser Thr Lys
        115                 120                 125
Gly Pro Ser Val Phe Pro Leu Ala Pro Cys Ser Arg Ser Thr Ser Glu
    130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Asn Phe Gly Thr Gln Thr Tyr Thr Cys Asn
        195                 200                 205
Val Asp His Lys Pro Ser Asn Thr Lys Val Asp Lys Thr Val Glu Arg
    210                 215                 220
Lys Cys Cys Val Glu Cys Pro Pro Cys Pro Ala Pro Val Ala Gly
225                 230                 235                 240
Pro Ser Val Phe Leu Phe Pro Pro Lys Pro Lys Asp Thr Leu Met Ile
                245                 250                 255
```

Ser Arg Thr Pro Glu Val Thr Cys Val Val Asp Val Ser His Glu
        260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
        290                 295                 300

Val Val Ser Val Leu Thr Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 58
<211> LENGTH: 450
<212> TYPE: PRT
<213> ORGANISM: Artificial Sequence
<220> FEATURE:
<223> OTHER INFORMATION: Humanized heavy chains

<400> SEQUENCE: 58

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Val Lys Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Asp Arg Val Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Val Arg Lys Gly Ile Ile Tyr Asn Tyr Gly Ser Ser Asp Val Leu Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
            210                 215                 220

Lys Cys Cys Val Glu Cys Pro Pro Cys Pro Ala Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
            290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
            325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 59
<211> LENGTH: 450
<212> TYPE: PRT
<213> ORGANISM: Artificial Sequence
<220> FEATURE:
<223> OTHER INFORMATION: Humanized heavy chains

<400> SEQUENCE: 59

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Asp Arg Gly Thr Leu Thr Val Asp Thr Ser Ser Thr Ala Tyr
65                  70                  75                  80

Met Glu Leu Ser Ser Leu Arg Ser Glu Asp Thr Ala Val Tyr Phe Cys
            85                  90                  95

Val Arg Lys Gly Ile Ile Tyr Asn Tyr Gly Ser Ser Asp Val Leu Ala
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
            325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 60
<211> LENGTH: 450
<212> TYPE: PRT

<213> ORGANISM: Artificial Sequence
<220> FEATURE:
<223> OTHER INFORMATION: Humanized heavy chains

<400> SEQUENCE: 60

```
Gln Ile Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Asp Arg Gly Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Val Arg Lys Gly Ile Ile Tyr Asn Tyr Gly Ser Ser Asp Val Leu Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
```

```
                385                 390                 395                 400
Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly Lys
    450

<210> SEQ ID NO 61
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 61

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Tyr Met Asn Trp Val Arg Gln Ala Pro Gly Gln Ser Leu Glu Trp Ile
        35                  40                  45

Gly Asp Leu Asn Pro Asp Asn Gly Asp Thr Asn Tyr Asn Gln Lys Phe
    50                  55                  60

Val Gly Arg Val Thr Met Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Gly Lys Gly Gly Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
```

```
            290                 295                 300
Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 62
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 62

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ala Pro Gly Gln Ser Leu Glu Trp Ile
            35                  40                  45

Gly Asp Leu Asn Pro Asp Asn Gly Asp Thr Asn Tyr Asn Gln Lys Phe
        50                  55                  60

Val Gly Arg Val Thr Met Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Gly Lys Gly Gly Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
```

```
                210                 215                 220
Pro Cys Pro Ala Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
                290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 63
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 63

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ala Pro Gly Lys Ser Leu Glu Trp Ile
                35                  40                  45

Gly Asp Leu Asn Pro Asp Asn Gly Asp Thr Asn Tyr Asn Gln Lys Phe
                50                  55                  60

Val Gly Arg Ala Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Gly Lys Gly Phe Asp Tyr Trp Gly Gln Gly Thr Thr
                100                 105                 110

Leu Thr Val Ser Ser Ala Ser Thr Lys Gly Pro Ser Val Phe Pro Leu
                115                 120                 125

Ala Pro Cys Ser Arg Ser Thr Ser Glu Ser Thr Ala Ala Leu Gly Cys
```

```
            130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
                195                 200                 205

Thr Lys Val Asp Lys Thr Val Glu Arg Lys Cys Cys Val Glu Cys Pro
                210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 64
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 64

Glu Val Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
                20                  25                  30

Tyr Met Asn Trp Met Lys Gln Ser His Gly Lys Ser Leu Glu Trp Ile
                35                  40                  45

Gly Asp Leu Asn Pro Asp Asn Gly Asp Thr Asn Tyr Asn Gln Lys Phe
```

```
            50                  55                  60
Val Gly Arg Ala Thr Leu Thr Val Asp Lys Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Gly Gly Lys Gly Phe Asp Tyr Trp Gly Gln Gly Thr Thr
                100                 105                 110

Leu Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 65
<211> LENGTH: 443
<212> TYPE: PRT
<213> ORGANISM: Artificial Sequence
```

```
<220> FEATURE:
<223> OTHER INFORMATION: Humanized heavy chains

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Ile Asn Tyr
            20                  25                  30

Trp Val Gly Trp Val Arg Gln Ala Pro Gly Gln Gly Leu Glu Trp Met
        35                  40                  45

Gly Asp Val Tyr Pro Gly Gly Asn Tyr Thr Asn Asn Asn Glu Lys Leu
    50                  55                  60

Lys Gly Arg Val Thr Leu Thr Ala Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Lys Gly Arg Gly Gly Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400
```

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 66
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 66

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Leu Ile Asn Tyr
            20                  25                  30

Trp Val Gly Trp Val Arg Gln Ala Pro Gly Gln Gly Leu Glu Trp Ile
            35                  40                  45

Gly Asp Val Tyr Pro Gly Gly Asn Tyr Thr Asn Asn Asn Glu Lys Leu
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Lys Gly Arg Gly Gly Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

```
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 67
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 67

Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Ser Leu Ile Asn Tyr
            20                  25                  30
Trp Val Gly Trp Val Arg Gln Ala Pro Gly His Gly Leu Glu Trp Ile
        35                  40                  45
Gly Asp Val Tyr Pro Gly Gly Asn Tyr Thr Asn Asn Glu Lys Leu
    50                  55                  60
Lys Gly Arg Ala Thr Leu Thr Ala Asp Thr Ser Thr Ser Thr Ala Tyr
65                  70                  75                  80
Leu Glu Leu Ser Ser Leu Arg Ser Glu Asp Thr Ala Val Tyr Phe Cys
                85                  90                  95
Ala Arg Lys Gly Arg Gly Gly Met Asp Tyr Trp Gly Gln Gly Thr Thr
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
        195                 200                 205
Thr Lys Val Asp Lys Thr Val Glu Arg Lys Cys Cys Val Glu Cys Pro
    210                 215                 220
Pro Cys Pro Ala Pro Pro Val Ala Gly Pro Ser Val Phe Leu Phe Pro
225                 230                 235                 240
```

Pro Lys Pro Lys Asp Thr Leu Met Ile Ser Arg Thr Pro Glu Val Thr
            245                 250                 255

Cys Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
            290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
            325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 68
<211> LENGTH: 443
<212> TYPE: PRT
<213> ORGANISM: Artificial Sequence
<220> FEATURE:
<223> OTHER INFORMATION: Humanized heavy chains

<400> SEQUENCE: 68

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Ser Leu Ile Asn Tyr
            20                  25                  30

Trp Val Gly Trp Val Arg Gln Ala Pro Gly His Gly Leu Glu Trp Ile
            35                  40                  45

Gly Asp Val Tyr Pro Gly Gly Asn Tyr Thr Asn Asn Asn Glu Lys Leu
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Phe Cys
            85                  90                  95

Ala Arg Lys Gly Arg Gly Gly Met Asp Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

-continued

```
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
            195                 200                 205
Thr Lys Val Asp Lys Thr Val Glu Arg Lys Cys Cys Val Glu Cys Pro
    210                 215                 220
Pro Cys Pro Ala Pro Pro Val Ala Gly Pro Ser Val Phe Leu Phe Pro
225                 230                 235                 240
Pro Lys Pro Lys Asp Thr Leu Met Ile Ser Arg Thr Pro Glu Val Thr
            245                 250                 255
Cys Val Val Val Asp Val Ser His Glu Asp Pro Glu Val Gln Phe Asn
            260                 265                 270
Trp Tyr Val Asp Gly Val Glu Val His Asn Ala Lys Thr Lys Pro Arg
            275                 280                 285
Glu Glu Gln Phe Asn Ser Thr Phe Arg Val Val Ser Val Leu Thr Val
    290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
            325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
            405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440
```

ANTIBODIES THAT TARGET HUMAN CD47

CROSS REFERENCE TO RELATED APPLICATION

This application claims priority to U.S. Provisional Application No. 62/835,737, filed Apr. 18, 2019, the disclosure of which is incorporate by reference herein in its entirety.

INCORPORATION OF SEQUENCE LISTING

This application includes a Sequence Listing which is being submitted in ASCII format via EFS-Web, named "QLSF002US_ST25.txt," which is 98.7 KB in size and created on Apr. 17, 2020.

The contents of the Sequence Listing are incorporated herein by reference in their entirety.

BACKGROUND OF THE INVENTION

CD47 is a broadly expressed cell surface protein (also called integrin-associated protein), interacts with the myeloid inhibitory immunoreceptor SIRPα (also termed CD172a or SHPS-1). Engagement of SIRPα by CD47 negatively controls effector function of innate immune cells such as host cell phagocytosis (Steven E. Kauder et al, 2018). CD47 expression and/or activity have been implicated in a number of diseases and disorders. Accordingly, there exists a need for therapies that target CD47, as well as better methods for making such therapies.

CD47 and SIRP-α belong to the immunoglobulin superfamily and both conduct signaling inwards. SIRP-α is expressed on hematopoietic cells, including macrophages and dendritic cells, whilst CD47 is expressed ubiquitously (Murata et al., 2014), when it engages CD47 on a potential phagocytic target cell, phagocytosis is slowed or prevented. The CD47-SIRP-α interaction sends a "don't eat me" signal to the phagocytic cells. Therefore, blocking the CD47-SIRP-α interaction with a monoclonal antibody can provide an effective anti-cancerous treatment, i.e., increasing phagocytosis of CD47-expressing cells by macrophages (reviewed in Chao, et al, 2012 Curr Opin Immunol, 24(2): 225-32), for improved uptake and removal of cancer cells by the host's immune system. This mechanism is effective in leukemias, lymphomas, and many types of solid tumors. Furthermore, these CD47-blocking antibodies have been shown to synergize with other therapeutic antibodies including Rituxan® and Herceptin® in tumor models.

Various studies suggest that CD47 antibodies cause platelet aggregation and hemagglutination of the red blood cells. When different CD47-expressing cells bind a bivalent CD47 binding unit (e.g. Anti-CD47 antibody), they aggregate. This is an example of homotypic interactions. According to Uno S, Kinoshita Y, Azuma Y, et al, 2007 an anti-CD47 antibody has been reported to cause hemagglutination of erythrocytes. Likewise, the CD47 antibody, B6H12, has been reported by Dorahy et al, 1997, to cause direct platelet aggregation in some of the target subjects. Thus, a major drawback with existing CD47 targeting antibodies is induction of platelet aggregation and hemagglutination of RBCs.

The current clinical approved immunotherapies targeting CD47 have shown promising clinical results. However, the response rate of patients to these approved agents is still not satisfactory. As a result, there is a need in the art to identify a highly efficient anti-CD47 antibody which induces low or negative grade of hemagglutination and platelet aggregation. Such an antibody may be used alone or in combination with other therapeutic agents in drug treatment regimens.

SUMMARY OF THE INVENTION

The present disclosure provides isolated monoclonal anti-CD47 antagonist antibodies, and antigen-binding portions thereof that specifically bind to human CD47.

In an aspect of the invention, an isolated monoclonal anti-CD47 antagonist antibody, or antigen-binding portion thereof comprises a heavy chain variable region CDR3 comprising SEQ ID NO:22. In some embodiments, the monoclonal anti-CD47 antagonist antibody, or antigen-binding portion thereof further comprises a heavy chain variable region CDR1 comprising SEQ ID NO:16 and a heavy chain variable region CDR2 comprising SEQ ID NO:19. In preferred embodiments, the monoclonal anti-CD47 antagonist antibody, or antigen-binding portion thereof further comprises: (a) a light chain variable region CDR1 comprising SEQ ID NO:7; (b) a light chain variable region CDR2 comprising SEQ ID NO:10; and (c) a light chain variable region CDR3 comprising SEQ ID NO:13.

In one embodiment, the antibody or portion comprises a light chain variable region amino acid sequence having at least 95% identity to SEQ ID NO:1 and a heavy chain variable region amino acid sequence having at least 95% identity to SEQ ID NO:4. In another embodiment, the antibody or portion comprises a heavy chain variable region comprising an amino acid sequence that has at least 95%, at least 96%, at least 97%, at least 98%, or at least 99% identical to a sequence as set forth in SEQ ID NO:4.

In another aspect of the invention, an isolated monoclonal anti-CD47 antagonist antibody, or antigen-binding portion thereof comprises a heavy chain variable region CDR3 comprising SEQ ID NO:23. In some embodiments, the monoclonal anti-CD47 antagonist antibody, or antigen-binding portion thereof further comprises a heavy chain variable region CDR1 comprising SEQ ID NO:17 and a heavy chain variable region CDR2 comprising SEQ ID NO:20. In preferred embodiments, the monoclonal anti-CD47 antagonist antibody, or antigen-binding portion thereof further comprises: (a) a light chain variable region CDR1 comprising SEQ ID NO:8; (b) a light chain variable region CDR2 comprising SEQ ID NO:11; and (c) a light chain variable region CDR3 comprising SEQ ID NO:14.

In one embodiment, the antibody or portion comprises a light chain variable region amino acid sequence having at least 95% identity to SEQ ID NO:2 and a heavy chain variable region amino acid sequence having at least 95% identity to SEQ ID NO:5. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:5.

In another aspect of the invention, an isolated monoclonal anti-CD47 antagonist antibody, or antigen-binding portion thereof comprises a heavy chain variable region CDR3 comprising SEQ ID NO:24. In some embodiments, the monoclonal anti-CD47 antagonist antibody, or antigen-binding portion thereof further comprises a heavy chain variable region CDR1 comprising SEQ ID NO:18 and a heavy chain variable region CDR2 comprising SEQ ID NO:21. In preferred embodiments, the monoclonal anti-CD47 antagonist antibody, or antigen-binding portion thereof further comprises: (a) a light chain variable region CDR1 comprising SEQ ID NO:9; (b) a light chain variable region CDR2 comprising SEQ ID NO:12; and (c) a light chain variable region CDR3 comprising SEQ ID NO:15.

In one embodiment, the antibody or portion comprises a light chain variable region amino acid sequence having at least 95% identity to SEQ ID NO:3 and a heavy chain variable region amino acid sequence having at least 95% identity to SEQ ID NO:6. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:6.

In another aspect of the invention, an isolated monoclonal anti-CD47 antagonist antibody or an antigen-binding portion thereof comprises a heavy chain variable region comprising an amino sequence selected from the group consisting of SEQ ID NOs:35-38 and a light chain variable region comprising an amino sequence selected from the group consisting of SEQ ID NOs:25-27 In another aspect of the invention, an isolated monoclonal anti-CD47 antagonist antibody or an antigen-binding portion thereof comprises: a heavy chain variable region comprising an amino sequence selected from the group consisting of SEQ ID NOs: 39-42 and a light chain variable region comprising an amino sequence selected from the group consisting of SEQ ID NOs:28-31.

In another aspect of the invention, an isolated monoclonal anti-CD47 antagonist antibody or an antigen-binding portion thereof comprises: a heavy chain variable region comprising an amino sequence selected from the group consisting of SEQ ID NOs: 43-46 and a light chain variable region comprising an amino sequence selected from the group consisting of SEQ ID NOs:32-34.

The antibodies of the disclosed invention can be further engineered into formats suitable for human therapeutics by modifications that minimize immunogenicity. Suitable antibodies include, but are not limited to chimeric antibodies and humanized antibodies. The affinity, stability and specificity of the disclosed antibodies can also be further optimized by techniques known to one of skill in the art. Other formats can involve oligomerization, drug conjugation and fusion of the disclosed antibodies with other functional proteins.

The antibodies of the disclosed invention can be, for example, full-length antibodies, for example of an IgG1, IgG2, IgG3, or IgG4 isotype. Alternatively, the disclosed antibodies can be antibody fragments, such as Fab, Fab' and F(ab')$_2$ fragments, diabody, triabody, tetrabody, single-chain variable region fragment (scFv), disulfide-stabilized variable region fragment (dsFv), and half antibodies. Alternatively, the disclosed antibodies can be bispecific antibodies.

In another aspect of the invention, an isolated monoclonal antibody or antigen binding portion thereof comprises a light chain comprises an amino acid sequence selected from the group consisting of SEQ ID NOs: 47-56 and a heavy chain comprising an amino acid sequence selected from the group consisting of SEQ ID NOs: 57-68.

In some embodiments, the anti-CD47 antagonist antibody, or antigen-binding portion thereof binds to and blocks human CD47. Therefore, the antibody or antigen-binding portion can stimulate an anti-tumor immune response. In some embodiments, the anti-CD47 antagonist antibody, or antigen-binding portion thereof binds to and blocks CD47.

In another aspect of the invention, a composition comprising the isolated anti-CD47 antagonist monoclonal antibody, or antigen-binding portion thereof is also provided.

In another aspect of the invention, a pharmaceutical composition comprising the isolated anti-CD47 antagonist monoclonal antibody, or antigen-binding portion thereof and a pharmaceutically acceptable carrier are also provided. Compositions comprising an immunoconjugate of the invention and a pharmaceutically acceptable carrier are also provided.

In another aspect of the invention, a vector comprising an isolated nucleic acid molecule encoding the antibody, or antigen-binding portion thereof, and a host cell comprising an expression vector comprising said nucleic acid molecule are also provided.

The present invention further provides a method of stimulating immune responses using the anti-CD47 antagonist antibodies of the disclosed invention. For example, in one embodiment, the disclosed invention provides a method for treating a subject in need thereof, comprising the step of administering to the subject an effective amount of the antibody or antigen-binding portion of the disclosed invention.

In another aspect, the disclosed invention provides a method for treating cancer in a human comprising the step of administering to the human the anti-CD47 antagonist antibody or antigen-binding portion of the disclosed invention in an amount effective to treat said cancer.

In another aspect, the disclosed invention provides a method for treating infectious diseases in a human comprising the step of administering to the human the anti-CD47 antagonist antibody or antigen-binding portion of the disclosed invention in an amount effective to treat said infectious diseases.

Other features and advantages of the instant disclosure will be apparent from the following detailed description and examples, which should not be construed as limiting. The contents of all references, GenBank entries, patents and published patent applications cited throughout this application are expressly incorporated herein by reference.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
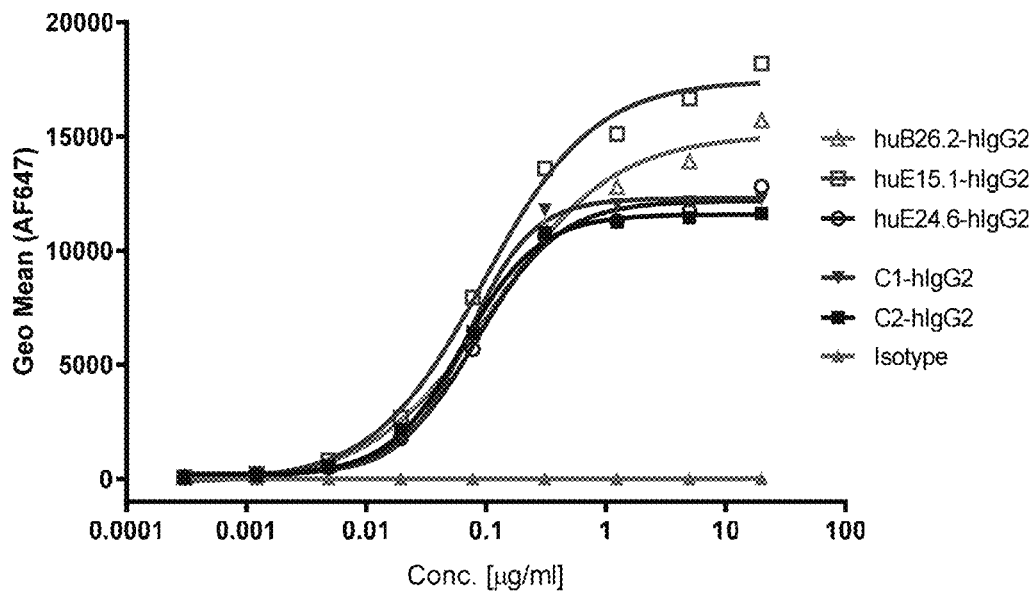
FIG. 1 shows humanized anti-CD47 antibodies bind to human MM.1S cancer cells.

The following embodiments and aspects thereof are described and illustrated in conjunction with systems, compositions and methods which are meant to be exemplary and illustrative, not limiting in scope.

Definitions

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "about" refers to a measurable value such as an amount, a time duration, and the like, and encompasses variations of ±20%, ±10%, 5%, 1%, 0.5% or ±0.1% from the specified value.

The term "epitope" as used herein can include any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the equilibrium dissociation constant is <1 M, preferably <100 nM and most preferably <10 nM.

The term "$K_D$" can refer to the equilibrium dissociation constant of a particular antibody-antigen interaction.

The term "immune response" as used herein can refer to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from an organism of invading pathogens, cells or tissues infected with pathogens, cancerous cells, or, in cases of autoimmunity or pathological inflammation, normal organismal cells or tissues.

An "antigen-specific T cell response" as used herein can refer to responses by a T cell that result from stimulation of the T cell with the antigen for which the T cell is specific. Non-limiting examples of responses by a T cell upon antigen-specific stimulation include proliferation and cytokine production (e.g., IL-2 production).

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc region". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single region antibodies, chimeric antibodies, diabodies and polypeptides that contain at least a portion of an immunoglobulin that is sufficient to confer specific antigen binding to the polypeptide. The Fc region includes portions of two heavy chains contributing to two or three classes of the antibody. The Fc region may be produced by recombinant DNA techniques or by enzymatic (e.g. papain cleavage) or via chemical cleavage of intact antibodies.

The term "antibody fragment," as used herein, refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 regions; (ii) the Fab' fragment, which is a Fab fragment having one or more cysteine residues at the C-terminus of the CH1 region; (iii) the Fd fragment having VH and CH1 regions; (iv) the Fd' fragment having VH and CH1 regions and one or more cysteine residues at the C-terminus of the CH1 region; (v) the Fv fragment having the VL and VH regions of a single arm of an antibody; (vi) the dAb fragment (Ward et al., Nature 341, 544-546 (1989)) which consists of a VH region; (vii) isolated CDR regions; (viii) F(ab')2 fragments, a bivalent fragment including two Fab' fragments linked by a disulfide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable region (VH) connected to a light chain variable region (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

"Single-chain variable fragment", "single-chain antibody variable fragments" or "scFv" antibodies as used herein refers to forms of antibodies comprising the variable regions of only the heavy (VH) and light (VL) chains, connected by a linker peptide. The scFvs are capable of being expressed as a single chain polypeptide. The scFvs retain the specificity of the intact antibody from which it is derived. The light and heavy chains may be in any order, for example, VH-linker-VL or VL-linker-VH, so long as the specificity of the scFv to the target antigen is retained.

An "isolated antibody", as used herein, can refer to an antibody that is substantially free of other antibodies having different antigenic specificities (e.g., an isolated antibody that specifically binds a CD47 protein can be substantially free of antibodies that specifically bind antigens other than CD47 proteins). An isolated antibody that specifically binds a human CD47 protein can, however, have cross-reactivity to other antigens, such as CD47 proteins from other species. Moreover, an isolated antibody can be substantially free of other cellular material and/or chemicals.

Anti-CD47 antagonist antibody-producing cells, e.g., hybridomas, can be selected, cloned and further screened for desirable characteristics, including robust growth, high antibody production and desirable antibody characteristics. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

The terms "monoclonal antibody" or "monoclonal antibody composition" as used herein can refer to a preparation of antibody molecules of single molecular composition. A monoclonal antibody composition displays a single binding specificity and affinity for a particular epitope.

The term "recombinant human antibody", as used herein, can refer to all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" can refer to the antibody class (e.g., IgM or IgG1) that is encoded by the heavy chain constant region genes. An antibody can be an immunoglobulin G (IgG), an IgM, an IgE, an IgA or an IgD molecule, or is derived therefrom.

The phrases "an antibody recognizing an antigen" and "an antibody specific for an antigen" are used interchangeably herein with the term "an antibody which binds specifically to an antigen."

As used herein, an antibody that "specifically binds human CD47" can refer to an antibody that binds to a human CD47 protein (and possibly a CD47 protein from one or more non-human species) but does not substantially bind to non-CD47 proteins. Preferably, the antibody binds to a human CD47 protein with "high affinity," namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less.

The term "does not substantially bind" to a protein or cells, as used herein, can mean that it cannot bind or does not bind with a high affinity to the protein or cells, i.e., binds to the protein or cells with an $K_D$ of $2\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "high affinity" for an IgG antibody can refer to an antibody having a $K_D$ of $1\times10^{-6}$ M or less, preferably $1\times10^{-7}$ M or less, more preferably $1\times10^{-8}$ M or less, even more preferably $1\times10^{-9}$ M or less, even more preferably $1\times10^{-10}$ M or less for a target antigen. However, "high affinity" binding can vary for other antibody isotypes.

The term "pharmaceutical formulation" refers to a preparation which is in such form as to permit the biological activity of an active ingredient contained therein to be effective, and which contains no additional components which are unacceptably toxic to a subject to which the formulation would be administered.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmaco-dynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

An "antagonist antibody" as used herein, is an antibody blocks or dampens a biological response by binding to and blocking a receptor (for example, CD47) to which the antibody binds. An antagonist may, for example, inhibit a receptor's phosphorylation due to binding of the receptor to a ligand or may inhibit the signal/cells activation. In one embodiment, the antibodies of the invention are antagonistic anti-CD47 antibodies.

A "CDR grafted antibody" is an antibody comprising one or more CDRs derived from an antibody of a particular species or isotype and the framework of another antibody of the same or different species or isotype.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant regions of the heavy and/or light chains of the non-human species antibody are mutated to produce the humanized antibody. In another embodiment, the constant region(s) from a human antibody are fused to the variable region(s) of a non-human species. In another embodiment, a humanized antibody is a CDR grafted antibody comprising one or more CDRs derived from an antibody of a particular species or isotype and the framework of human antibodies. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" (cAb) refers to an antibody that contains one or more regions from one antibody and one or more regions from one or more other antibodies. In one embodiment, one or more of the CDRs are derived from a human anti-CD47 antibody. In another embodiment, all of the CDRs are derived from a human anti-CD47 antibody. In another embodiment, the CDRs from more than one human anti-CD47 antibodies are mixed and matched in a chimeric antibody. For instance, a chimeric antibody may comprise a CDR1 from the light chain of a first human anti-CD47 antibody, a CDR2 and a CDR3 from the light chain of a second human anti-CD47 antibody, and the CDRs from the heavy chain from a third anti-CD47 antibody. In the context of the present disclosure, cAbs represent variable regions of mouse monoclonal antibodies fused to the Fc regions of human antibodies. In another embodiment, other combinations are also possible.

The term "subject" can refer to any human or non-human animal. The subject can be male or female and can be any suitable age, including infant, juvenile, adolescent, adult, and geriatric subjects. The term "nonhuman animal" includes all vertebrates, e.g., mammals and non-mammals, such as nonhuman primates, sheep, dogs, cats, cows, horses, chickens, rabbits, mice, rats, amphibians, and reptiles, although mammals are preferred, such as non-human primates, sheep, dogs, cats, cows and horses.

The binding of an antibody of the disclosed invention to CD47 can be assessed using one or more techniques well established in the art. For example, in a preferred embodiment, an antibody can be tested by ELISA assays, for example using a recombinant CD47 protein. Still other suitable binding assays include but are not limited to a flow cytometry assay in which the antibody is reacted with a cell line that expresses human CD47, such as Expi293 or ExpiCHO cells that have been transfected to express CD47 (e.g., human CD47) on their cell surface. Additionally or alternatively, the binding of the antibody, including the binding kinetics (e.g., $K_D$ value) can be tested in BIAcore binding assays, Octet Red96 (Pall) and the like.

Preferably, an antibody of the disclosed invention binds to a human CD47 protein with a $K_D$ of $5\times10^{-8}$ M or less, binds to a human CD47 protein with a $K_D$ of $2\times10^{-8}$ M or less, binds to a human CD47 protein with a $K_D$ of $5\times10^{-9}$ M or less, binds to a human CD47 protein with a $K_D$ of $4\times10^{-9}$ M or less, binds to a human CD47 protein with a $K_D$ of $3\times10^{-9}$ M or less, binds to a human CD47 protein with a $K_D$ of $2\times10^{-9}$ M or less, binds to a human CD47 protein with a $K_D$ of $1\times10^{-9}$ M or less.

The present disclosure relates to isolated monoclonal antibodies, or antigen binding portions thereof, which binds to and blocks CD47, and uses thereof. In certain embodiments, the antibodies of the disclosed invention are derived from identified heavy and light chain germline sequences and/or comprise identified structural features such as CDR regions comprising identified amino acid sequences. This disclosure provides isolated antibodies, methods of making such antibodies and antigen-binding portions thereof of the disclosed invention. This disclosure also relates to methods of using the antibodies, such as using the anti-CD47 antagonist antibodies of the disclosed invention to stimulate immune responses, alone or in combination with other immunostimulatory or therapeutic antibodies. Accordingly, also provided are methods of using the anti-CD47 antagonist antibodies of the disclosed invention for example, including but not limited to, treating cancer in a human. Various aspects of the invention relate to antibodies and antibody fragments, pharmaceutical compositions, nucleic acids, recombinant expression vectors, and host cells for making such antibodies and fragments. Methods of using the antibodies of the invention to detect human CD47, to stimulate CD47 activity, either in vitro or in vivo, and to prevent or treat disorders such as cancer are also encompassed by the invention.

Complementarity determining regions (CDRs) are known as hypervariable regions both in the light chain and the heavy chain variable regions. The more highly conserved portions of variable regions are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable region sequences that is applicable to any antibody. One of ordinary skill in the art can unambiguously assign this system of "Kabat numbering" to any variable region amino acid sequence, without reliance on any experimental data beyond the sequence itself.

In certain embodiments, the present invention provides anti-CD47 antagonist antibodies or antigen-binding portions thereof. In one embodiment, the mouse antibody or portion comprises (a) a light chain variable region CDR1 comprising SEQ ID NO:7, SEQ ID NO:8, SEQ ID NO:9; (b) a light chain variable region CDR2 comprising SEQ ID NO:10, SEQ ID NO:11, SEQ ID NO:12; (c) a light chain variable region CDR3 comprising SEQ ID NO:13, SEQ ID NO:14, SEQ ID NO:15; (d) a heavy chain variable region CDR1 comprising SEQ ID NO:16, SEQ ID NO:17, SEQ ID NO:18; (e) a heavy chain variable region CDR2 comprising SEQ ID NO:19, SEQ ID NO:20, SEQ ID NO:21; (f) a heavy chain variable region CDR3 comprising SEQ ID NO:22, SEQ ID NO:23, SEQ ID NO:24.

In one embodiment, the present disclosure provides a monoclonal antibody or antigen-binding portion thereof that binds to a CD47 epitope, that comprises a light chain variable region amino acid sequence having at least 95% identity to SEQ ID NOs: 1, 25, 26 or 27; and a heavy chain variable region amino acid sequence having at least 95% identity to SEQ ID NOs:4, 35, 36, 37, 38.

In another embodiment, the present disclosure provides a monoclonal antibody or antigen-binding portion thereof that binds to a CD47 epitope, that comprises a light chain variable region amino acid sequence having at least 95% identity to SEQ ID NOs: 2, 28, 29, 30 or 31; and a heavy chain variable region amino acid sequence having at least 95% identity to SEQ ID NOs:5, 39, 40, 41 or 42.

In yet another embodiment, the present disclosure provides a monoclonal antibody or antigen-binding portion thereof that binds to a CD47 epitope, that comprises a light chain variable region amino acid sequence having at least 95% identity to SEQ ID NOs: 3, 32, 33 or 34 and a heavy chain variable region amino acid sequence having at least 95% identity to SEQ ID NOs:6, 43, 44, 45 or 46.

Given that each of these antibody Fab can bind to human CD47, the VH and VL sequences can be "mixed and matched" to create other anti-CD47 binding molecules of the invention.

Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence.

In some embodiments, the humanized antibody or antigen binding portion thereof comprises a heavy chain variable region comprising an amino acid sequence selected from the group consisting of SEQ ID NOs: 35-38 and a light chain variable region comprising an amino acid sequence selected from the group consisting of SEQ ID NOs: 25-27. Preferred heavy and light chain combinations include but not limited to:

(a) a heavy chain variable region comprising the amino acid sequence of SEQ ID NO:35 and a light chain variable region comprising the amino acid sequence of SEQ ID NO:25;

(b) a heavy chain variable region comprising the amino acid sequence of SEQ ID NO:36 and a light chain variable region comprising the amino acid sequence of SEQ ID NO:26;

(c) a heavy chain variable region comprising the amino acid sequence of SEQ ID NO:37 and a light chain variable region comprising the amino acid sequence of SEQ ID NO:27;

(d) a heavy chain variable region comprising the amino acid sequence of SEQ ID NO:38 and a light chain variable region comprising the amino acid sequence of SEQ ID NO:27;

In some embodiments, the humanized antibody or antigen binding portion thereof comprises a heavy chain variable region comprising an amino acid sequence selected from the group consisting of SEQ ID NOs:39-42 and a light chain variable region comprising an amino acid sequence selected from the group consisting of SEQ ID NOs:28-31. Preferred heavy and light chain combinations include but not limited to:

(a) a heavy chain variable region comprising the amino acid sequence of SEQ ID NO:39 and a light chain variable region comprising the amino acid sequence of SEQ ID NO:28;

(b) a heavy chain variable region comprising the amino acid sequence of SEQ ID NO:40 and a light chain variable region comprising the amino acid sequence of SEQ ID NO:29;

(c) a heavy chain variable region comprising the amino acid sequence of SEQ ID NO:41 and a light chain variable region comprising the amino acid sequence of SEQ ID NO:30;

(d) a heavy chain variable region comprising the amino acid sequence of SEQ ID NO:42 and a light chain variable region comprising the amino acid sequence of SEQ ID NO:31;

In some embodiments, the humanized anti-CD47 antagonist antibody or antigen binding portion thereof comprises a light chain comprising an amino acid sequence selected from the group consisting of SEQ ID NOs: 32-34 and a heavy chain comprising an amino acid sequence selected from the group consisting of SEQ ID NOs: 43-46. Preferred heavy and light chain combinations include but not limited to:

(a) a heavy chain variable region comprising the amino acid sequence of SEQ ID NO:43 and a light chain variable region comprising the amino acid sequence of SEQ ID NO:32;

(b) a heavy chain variable region comprising the amino acid sequence of SEQ ID NO:44 and a light chain variable region comprising the amino acid sequence of SEQ ID NO:33;

(c) a heavy chain variable region comprising the amino acid sequence of SEQ ID NO:45 and a light chain variable region comprising the amino acid sequence of SEQ ID NO:34;

(d) a heavy chain variable region comprising the amino acid sequence of SEQ ID NO:46 and a light chain variable region comprising the amino acid sequence of SEQ ID NO:34;

In some embodiments, the humanized anti-CD47 antagonist antibody or antigen binding portion thereof comprises a light chain comprising an amino acid sequence selected from the group consisting of SEQ ID NOs:47-56 and a heavy chain comprising an amino acid sequence selected from the group consisting of SEQ ID NOs:57-68.

In one embodiment, the invention provides an anti-CD47 antibody, or an antigen-binding fragment thereof, comprising a heavy chain comprising a CDR3 region as set forth in SEQ ID NOs: 22, and comprising a heavy chain variable region comprising an amino acid sequence that has at least 95%, at least 96%, at least 97%, at least 98%, or at least 99% identical to a sequence as set forth in any one of SEQ ID NOs:4, 35-38 and 57-60.

In one embodiment, the invention provides an anti-CD47 antibody, or an antigen-binding fragment thereof, comprising a heavy chain comprising a CDR3 region as set forth in SEQ ID NOs: 23, and comprising a heavy chain variable region comprising an amino acid sequence that has at least 95%, at least 96%, at least 97%, at least 98%, or at least 99% identical to a sequence as set forth in any one of SEQ ID NOs:5, 39-42 and 61-64.

In one embodiment, the invention provides an anti-CD47 antibody, or an antigen-binding fragment thereof, comprising a heavy chain comprising a CDR3 region as set forth in SEQ ID NOs: 24, and comprising a heavy chain variable region comprising an amino acid sequence that has at least 95%, at least 96%, at least 97%, at least 98%, or at least 99% identical to a sequence as set forth in any one of SEQ ID NOs:6, 43-46 and 65-68.

In one embodiment, the invention provides an anti-CD47 antibody, or an antigen-binding fragment thereof, comprising a light chain comprising a CDR3 region as set forth in SEQ ID NOs:13, and having a light chain variable region comprising an amino acid sequence that has at least 95%, at least 96%, at least 97%, at least 98%, or at least 99% identical to a sequence as set forth in any one of SEQ ID NOs: 1, 25-27 and 47-49.

In one embodiment, the invention provides an anti-CD47 antibody, or an antigen-binding fragment thereof, comprising a light chain comprising a CDR3 region as set forth in SEQ ID NOs:14, and having a light chain variable region comprising an amino acid sequence that has at least 95%, at least 96%, at least 97%, at least 98%, or at least 99% identical to a sequence as set forth in any one of SEQ ID NOs: 2, 28-31 and 50-53.

In one embodiment, the invention provides an anti-CD47 antibody, or an antigen-binding fragment thereof, comprising a light chain comprising a CDR3 region as set forth in SEQ ID NOs:15, and having a light chain variable region comprising an amino acid sequence that has at least 95%, at least 96%, at least 97%, at least 98%, or at least 99% identical to a sequence as set forth in any one of SEQ ID NOs: 3, 32-34 and 54-56.

Thus, in certain embodiments, the CDR3 region is held constant, while variability may be introduced into the remaining CDRs and/or framework regions of the heavy and/or light chains, while the antibody, or antigen binding fragment thereof, retains the ability to bind to CD47 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those skilled in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. In addition to chemically-conserved amino acids, substitutions may include any amino acid which occurs in similar positions within related evolutionary-conserved human variable heavy chain sequences, human variable light chain sequences, and orthologous sequences from non-human species.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Examples

The following examples are not intended to limit the scope of the claims to the invention, but is rather intended to be exemplary of certain embodiments. Any variations in the exemplified methods which occur to the skilled artisan are intended to fall within the scope of the present invention.

Vector Construction:

Vector pcDNA3.4TOPO (Invitrogen) was ligated to a short polylinker containing EcoRI, XhoI, and NotI. The resulting plasmid was digested with EcoRI and NotI restriction enzymes and purified by gel electrophoresis. For heavy chain cloning, we assembled using Gibson assembly the prepared vector, a gblock encoding and VH region (IDT), and human IgG2 gblock encoding an XhoI site at the junction of the J-chain and CH1 domain. The plasmid was prepared and digested with EcoRI and XhoI to accommodate all the humanized variable heavy (VH) domains with an IgG2 isotype. All assembly was done with the Gibson method (NEB). Variable light regions were constructed with a similar method using gblocks to assemble Vkappa regions with a gblock fragment which encoded the constant kappa (Ck).

Protein Expression, Purification, and Binding Characterization:

Plasmids were prepped and transfected into Expi293 or ExpiCHO cells using the transient expression system (Thermo Fisher). Briefly plasmids were transfected into 3e6 cells/ml cells at 1 μg plasmid DNA total/ml culture. Heavy chain and light chain plasmids were mixed in a 1:1 ratio. Cultures were incubated at 37° C., shaking. After 16 hours, we added Transfection Enhancer 1 and 2 to the cultures and continued incubation for six days. Supernatant were filtered, and protein titers were determined by an IgG quantitation protocol using the Octet Red96 (Pall). IgG was purified by Mab Select Sure Protein-A column purification on an ACTA PURE system and dialyzed overnight in PBS. Purified antibodies were characterized for affinity to the antigen by Octet Red96 by loading purified antibodies onto anti-human Heavy Chain (AHC) capture sensors and measuring rates of association and dissociation of CD47 histidine tagged target at three concentrations. (Table 1).

TABLE 1

Mono-valent binding kinetics of humanized anti-CD47 Antibodies were compared to benchmark controls and mouse hybridomas, as determined by Octet.

| Subclone Name | KD [nM] | kon (1/Ms) | Kdis (1/s) | T1/2 life (mm) |
|---|---|---|---|---|
| 47AR.B26.10-mIgG1 | 6.1 | 9.90E+05 | 6.00E−03 | 1.9 |
| 47QL.E15.1-mIgG2a | 4.9 | 7.10E+05 | 3.50E−03 | 3.3 |
| 47QL.E24.6-mIgG1 | 3.4 | 6.10E+05 | 2.10E−03 | 5.5 |
| huB26.2-hIgG2 | 8.9 | 7.00E+05 | 6.30E−03 | 1.8 |
| huE15.1-hIgG2 | 6.7 | 6.60E+05 | 4.50E−03 | 2.6 |
| huE24.6-hIgG2 | 8.4 | 3.60E+05 | 3.10E−03 | 3.7 |
| C1-hIgG2 | 17 | 2.40E+05 | 4.00E−03 | 2.9 |
| C2-hIgG2 | 38 | 3.10E+05 | 1.20E−02 | 1 |

FlowCytometry

Human/Cyno CD47 transfected CHO cells were harvested by Accutase treatment, washed with media and incubated with serial diluted anti-CD47 antibodies in FACS buffer (DPBS+2% FBS+0.05% sodium azide) followed by AF647-labeled F(ab')2 goat anti-human IgG and 7-AAD. Stained samples were analyzed using FlowJo by gating on FSC/SSC, followed by live/dead cell gating, and CD47+ cells (mean fluorescence intensity Geometric Mean) (Table 2).

MM.1S cells (ATCC CRL-2974) were dissociated by pipetting cells, washed with media and incubated with serial diluted anti-CD47 antibodies in FACS buffer (DPBS+2% FBS+0.05% sodium azide) followed by AF647-labeled F(ab')2 goat anti-human IgG and 7-AAD. Stained samples were analyzed using FlowJo by gating on FSC/SSC, followed by live/dead cell gating, and CD47+ cells (mean fluorescence intensity Geometric Mean) (FIG. 1, Table 2).

TABLE 2

Anti-CD47 Hybridomas Bind to Human Cancer Cell Lines.

| | Cell Binding (EC50 ug/ml) | | | |
|---|---|---|---|---|
| | huCD47/ CHO | cynoCD47/ CHO | Raji | MM1S |
| 47AR.B26.10-mIgG1 | 0.132 | 0.13 | 0.123 | 0.14 |
| 47QL.E15.1-mIgG2a | 0.111 | 0.236 | 0.074 | 0.089 |

TABLE 2-continued

Anti-CD47 Hybridomas Bind to Human Cancer Cell Lines.

| | Cell Binding (EC50 ug/ml) | | | |
|---|---|---|---|---|
| | huCD47/CHO | cynoCD47/CHO | Raji | MM1S |
| 47QL.E24.6-mIgG1 | 0.208 | 0.306 | 0.145 | |
| cAb.B26.2-hIgG2 | 0.15 | 0.332 | 0.093 | 0.343 |
| cAb.E15.1-hIgG2 | 0.202 | 0.231 | 0.047 | 0.081 |
| cAb.E24.6-hIgG2 | 0.131 | 0.275 | 0.089 | 0.143 |
| huB26.2-hIgG2 | 0.202 | 0.49 | 0.185 | 0.363 |
| huE15.1-hIgG2 | 0.147 | 0.194 | 0.07 | 0.321 |
| huE24.6-hIgG2 | 0.242 | 0.155 | 0.057 | 0.194 |
| C1-hIgG2 | 0.187 | 0.195 | 0.103 | 0.105 |
| C2-hIgG2 | 0.852 | 0.633 | 0.3 | 0.625 |

SIRP Blocking Assay with Anti-CD47 Antibodies

Figure 2:
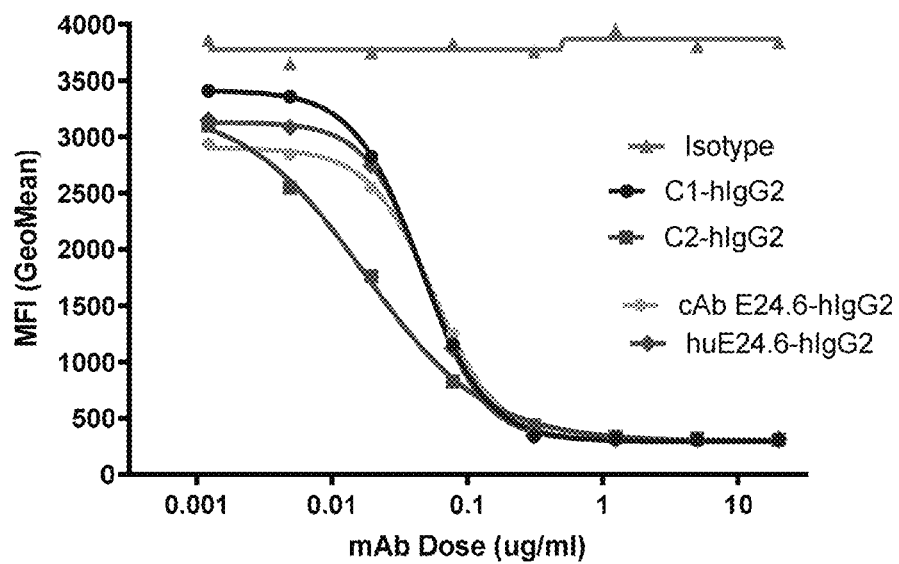
FIG. 2 shows anti-CD47 antibody E24.6 effectively blocked the binding of SIRPα to CD47.

CHO cells expressing human CD47 or Raji cells (ATCC CCL-86) were counted, washed with FACS buffer, and blocked with 20 ul human FcR Blocking reagent (Miltenyi Biotec cat #130-059-901) per 1E7 cells for 10 mins at room temperature. Cells were mixed with 1 µg/ml rh-SIRPα/Fc chimeric protein prior to mixing 1:1 with serial diluted anti-CD47 antibodies (20 ug/ml, 1:4 dilutions of antibodies purified from hybridomas, chimeric antibodies (cAb), or humanized antibodies (hu)), positive human IgG2 antibodies (C1 or C2), negative control IgG2 antibody (Isotype), or no antibody to observe SIRPα binding to CD47 on cells. Cells were incubated on ice for 20 minutes, washed twice with FACS buffer, and incubated 25 minutes in 1:500 diluted anti-hu IgG1 Fc PE secondary antibody in FACS buffer. Finally, samples were washed again and stained with 7-AAD (5 ul/1E6 cells) prior to flow cytometry analysis with a BD FACS Canto II or LSR Fortessa cell analyzer (FIG. 2, Table 3).

TABLE 3

Anti-CD47 antibodies effectively block the binding of SIRPa to CD47.

| | SIRPa Blocking IC50 (ug/ml) | |
|---|---|---|
| | huCD47/CHO | Raji |
| 47AR.B26.10-mIgG1 | 0.071 | 0.063 |
| 47QL.E15.1-mIgG2a | 0.155 | 0.018 |
| 47QL.E24.6-mIgG1 | 0.408 | 0.034 |
| cAb.B26.2-hIgG2 | | 0.059 |
| cAb.E15.1-hIgG2 | | 0.042 |
| cAb.E24.6-hIgG2 | | 0.056 |
| huB26.2-hIgG2 | | 0.115 |
| huE15.1-hIgG2 | | 0.034 |
| huE24.6-hIgG2 | | 0.05 |
| C1-hIgG2 | 0.252 | 0.062 |

Anti-CD47-Mediated Phagocytosis of CD47 Expressing Cells

Figure 3A:
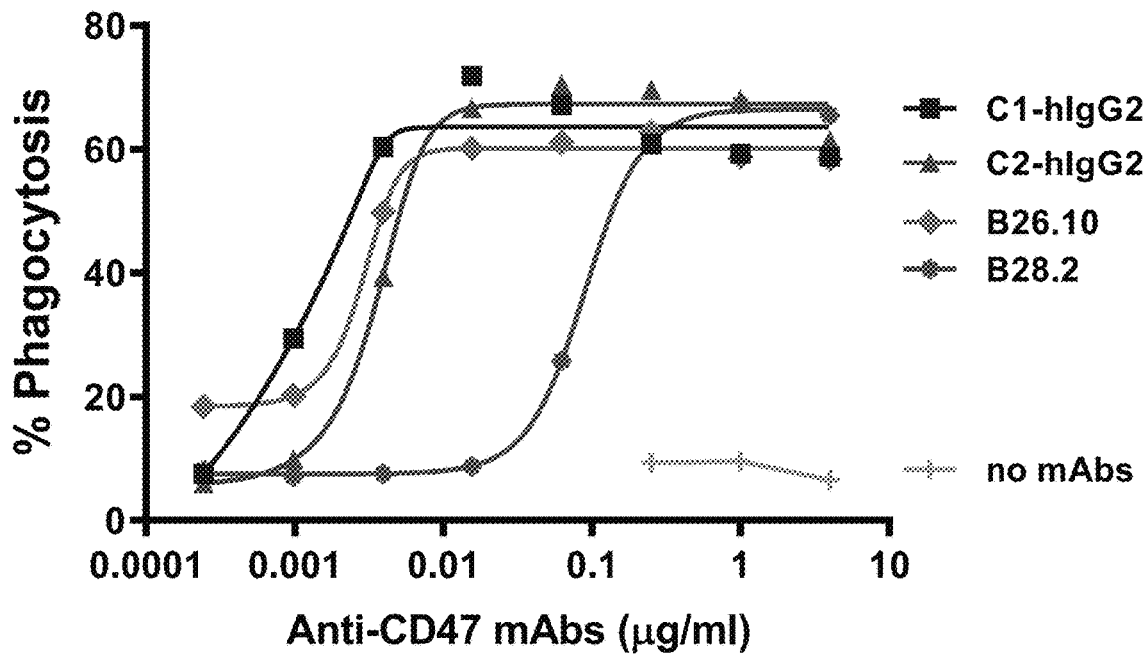
FIGS. 3A-3C show anti-CD47 antibodies purified from hybridomas induced phagocytosis of Raji tumor cells (FIG. 3A), MM1S cells (FIG. 3B), and SK-OV3 cells (FIG. 3C) by human monocyte-derived macrophages.
Figure 3B:
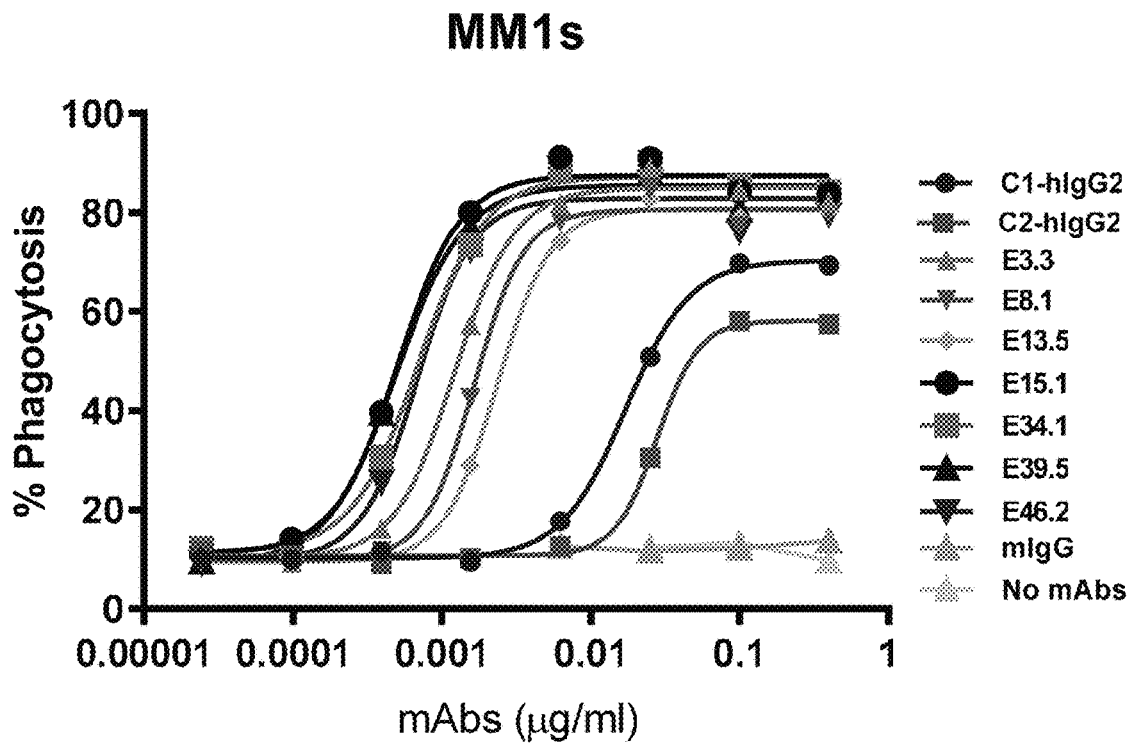
Figure 3C:
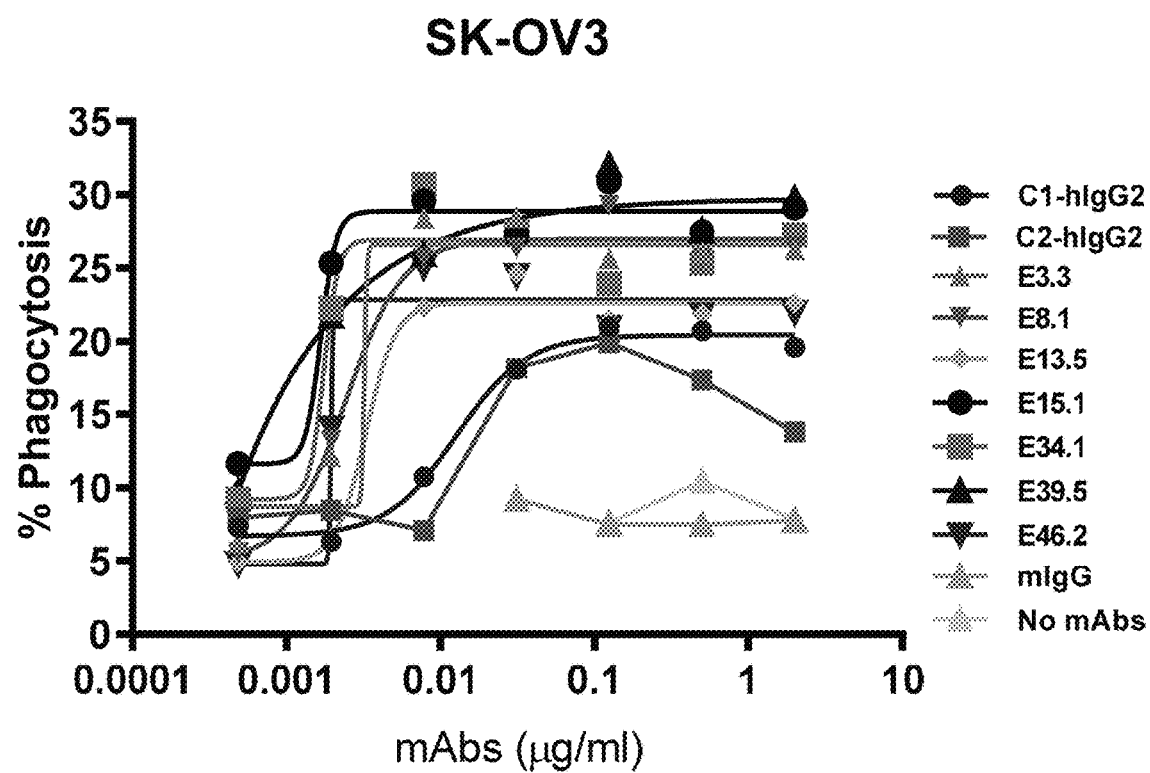
Figure 4A:
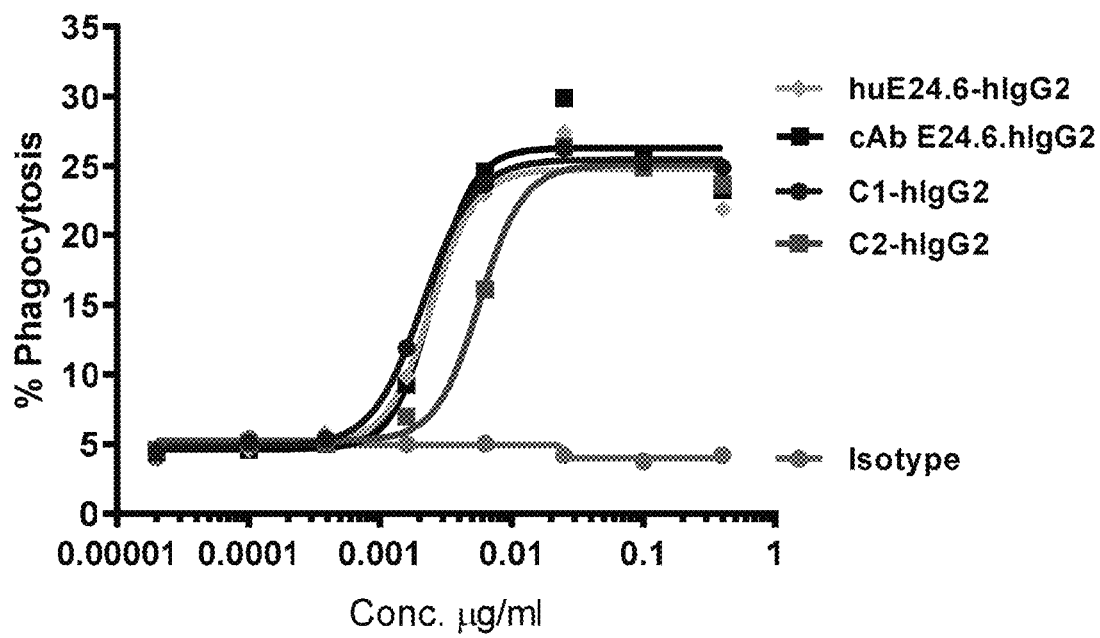
FIGS. 4A, 4B, and 4C show humanized and chimeric anti-CD47 antibodies induced phagocytosis of MM1S Cells.
Figure 4B:
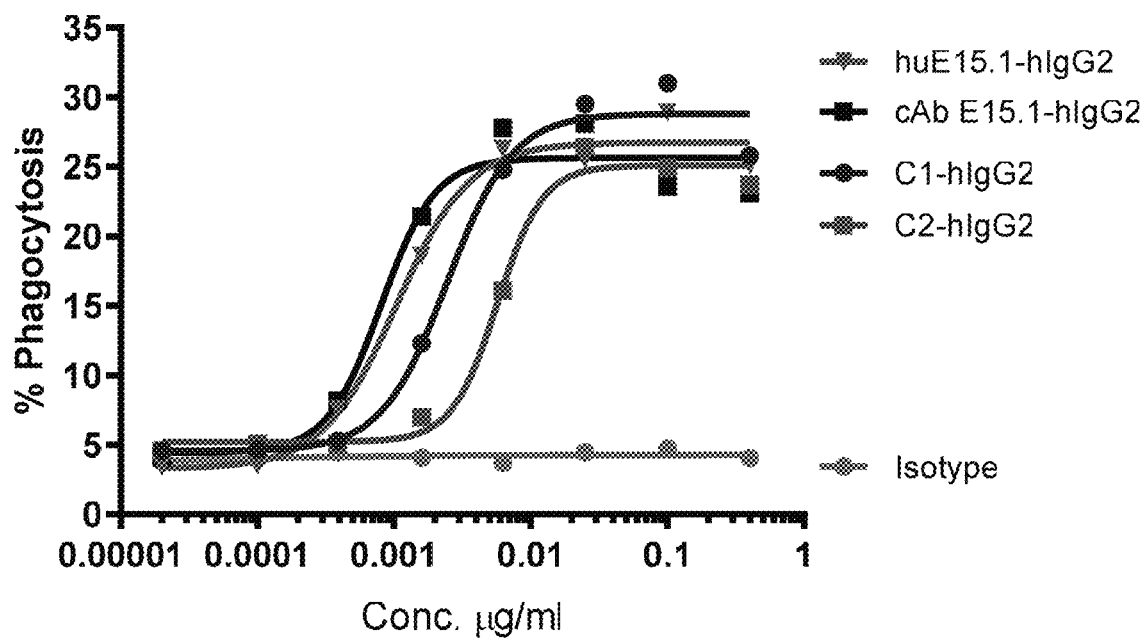
Figure 4C:
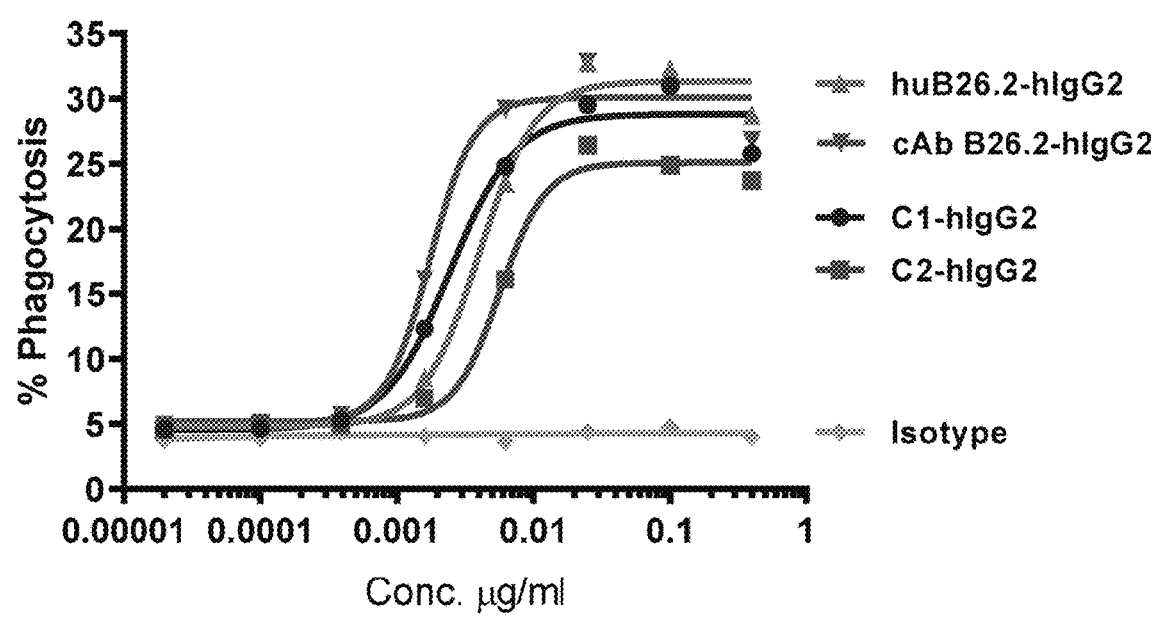

Mononuclear cells from human peripheral blood were prepared by density gradient centrifugation with Ficoll cell separation and quantified with a Vi-Cell XR cell counter. To separate monocytes, we incubated 1E8 cells for 2 hours in a T75 flask with RPMI-1640 media 10% Heat-inactivated FBS to allow monocytic cells to settle and attach. Non-adherent cells were removed, and the flask was incubated with media and 20 ng/ml recombinant human-M-CSF for 7 days, followed by media with 20 ng/ml rh-M-CSF and 10 ng/ml rh IL-10 for an additional 2 days. The monocyte-derived macrophages were washed, harvested by Trypsin-EDTA, resuspended in media and quantified. These macrophage cells were combined at 1:4 ratio (Effector to Target cells) with CFSE-labeled target cells (Raji, MM.1S, SK-OV3 cells) and test antibodies in a round bottom ultra-low attachment 96 well plate and incubated at 37° C. for 2 hours. The anti-CD47 antibodies (purified from hybridomas (FIG. 3), chimeric antibodies (FIG. 4 "cAb"), or humanized antibodies (FIG. 4, "hu"), positive (C1 or C2) controls, or negative (Isotype) controls were titrated in RPMI-1640+ 10% heat inactivated FBS media. Cells were resuspended by pipette and transferred to a V-bottom polypropylene plate for FACS staining with anti-CD36 APC (Thermo Fisher cat #MA1-10210) and 7-AAD in DPBS+20% FBS. Samples were analyzed using FlowJo by gating on FSC/SSC, followed by live/dead cell gating, and CFSE/APC double positives, which indicated that macrophages engulfed target cells (FIG. 3A, FIG. 3B, FIG. 3C, FIG. 4A, FIG. 4B, FIG. 4C).

Hemagglutination of Red Blood Cells for CD47

Figure 5:
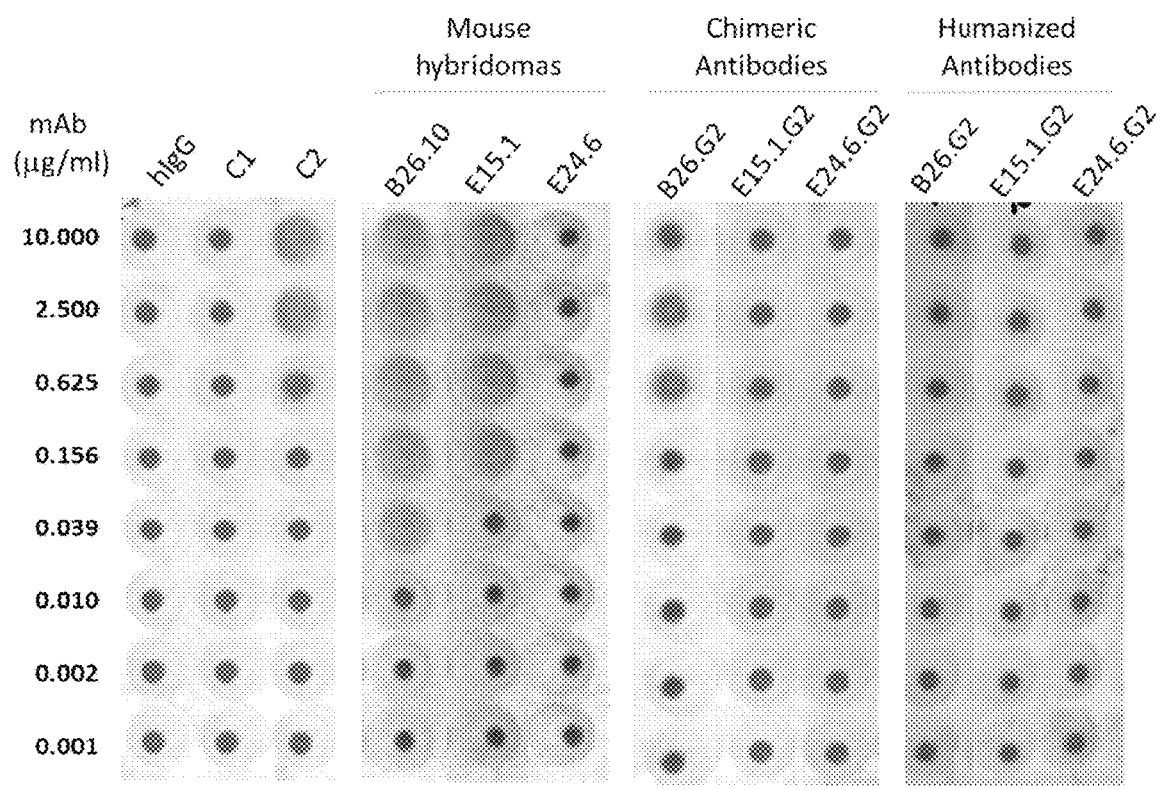
FIG. 5 shows that the lead anti-CD47 antibodies do not induce hemagglutination of red blood cells.

Red blood cells (RBC) were isolated from the bottom of the tube following purification of mononuclear cells from whole blood by density gradient centrifugation. The RBCs were washed 3 times with DPBS and prepared at 2E7 cells/ml with DPBS. Titrated anti-CD47 antibodies, positive (C1 or C2) controls, and negative (Isotype) controls in DPBS were mixed with equal volume RBCs in a round-bottom 96-well plate and incubated at room temperature for 2 hours. Hemagglutination analysis was done by image analysis of wells (FIG. 5).

SEQUENCE LISTING

Mouse Antibodies

SEQ ID NO: 1
DIVMSQSPSSLAVSVREKLTMSCKSSQSLLYSSNQKNYLAWYQQKPGQS

PKLLIYWASTRESGVPDRFTGSGSGTDFTLTISSVKAEDLAVYYCHQYY

SYPLTFGAGTKLELK

Underlined and bold: CDR1, 2 and 3, respectively (the same below), defined according to the Kabat numbering scheme.

SEQ ID NO: 2
DAVMTQTPLSLPVSLGDQASISCRSSQSLEKSNGNTYLNWYLQKPGQSP

QLLIYRVSRRYSGVLDRFSGSGSGTDFTLKISRVEAEDLGVYFCLQVTH

VPYTFGGGTRLEIK

SEQ ID NO: 3
DVLMTQTPLSLPVSLGDQASISCRSTQSIVHSNGKTYLEWYLQKPGQSP

KLLIYRVSNRFSGVPDRISGSGSGTDFTLKISRVETEDLGVYYCFQGSH

VPFTFGGGTKVEIK

SEQ ID NO: 4
QIQLQQSGPELVKPGASVKISCKASGYTFIDYYINWVKQRPGQGLEWIG

WIYPGSGNTKYNEKFKDKGTLTVDTSSSTAYMQLSSLTSEDSAVYFCVR

KGIIYNYGSSDVLAYWGQGTLVTVSA

```
                                      SEQ ID NO: 5
EVQLQQSGPELVKPGASVKISCKASGYTFTGYYMNWMKQSHGKSLEWIG
DLNPDNGDTNYNQKFVGKATLTVDKSSTAYMELRSLTSEDSAVYYCAR
GGKGGFDYWGQGTTLTVSS

SEQ ID NO: 6
QVQLQQSGTELVRPGTSVKISCKASGYSLINYWVGWVKQRPGHGLEWIG
DVYPGGNYTNNNEKLKGKATLTADTSASTAYLQLSSLTSEDSAVYFCAR
KGRGGMDYWGQGTSVTVSS
```

Light Chain CDRs
CDR1

```
                                      SEQ ID NO: 7
             KSSQSLLYSSNQKNYLA

SEQ ID NO: 8
             RSSQSLEKSNGNTYLN

SEQ ID NO: 9
             RSTQSIVHSNGKTYLE
```

CDR2

```
                                      SEQ ID NO: 10
                  WASTRES

SEQ ID NO: 11
                  RVSRRYS

SEQ ID NO: 12
                  RVSNRFS
```

CDR3

```
                                      SEQ ID NO: 13
                 HQYYSYPLT

SEQ ID NO: 14
                 LQVTHVPYT

SEQ ID NO: 15
                 FQGSHVPFT
```

Heavy Chain CDRs
CDR1

```
                                      SEQ ID NO: 16
                    DYYIN

SEQ ID NO: 17
                    GYYMN
```

```
                                      SEQ ID NO: 18
                    NYWVG
```

CDR2

```
                                      SEQ ID NO: 19
              WIYPGSGNTKYNEKFKD

SEQ ID NO: 20
              DLNPDNGDTNYNQKFVG

SEQ ID NO: 21
              DVYPGGNYTNNNEKLKG
```

CDR3

```
                                      SEQ ID NO: 22
                KGIIYNYGSSDVLAY

SEQ ID NO: 23
                    GGKGGFDY

SEQ ID NO: 24
                    KGRGGMDY
```

Humanized Light Chain Variable Domain

```
                                      SEQ ID NO: 25
DIVMTQSPDSLAVSLGERLTINCKSSQSLLYSSNQKNYLAWYQQKPGQP
PKLLIYWASTRESGVPDRFSGSGSGTDFTLTISSVQAEDVAVYYCHQYY
SYPLTFGQGTKLELK

SEQ ID NO: 26
DIVMTQSPDSLAVSLGERLTINCKSSQSLLYSSNQKNYLAWYQQKPGQS
PKWYWASTRESGVPDRFSGSGSGTDFTLTISSVQAEDVAVYYCHQYYSY
PLTFGQGTKLELK

SEQ ID NO: 27
DIVMTQSPSSLAVSLRERLTINCKSSQSLLYSSNQKNYLAWYQQKPGQS
PKLLIYWASTRESGVPDRFSGSGSGTDFTLTISSVKAEDVAVYYCHQYY
SYPLTFGQGTKLELK

SEQ ID NO: 28
DVVMTQSPLSLPVTLGQPASISCRSSQSLEKSNGNTYLNWFQQRPGQSP
QLLIYRVSRRYSGVPDRFSGSGSGTDFTLKISRVEAEDVGVYYCLQVTH
VPYTFGQGTRLEIK
```

SEQ ID NO: 29
DAVMTQSPLSLPVTLGQPASISCRSSQSLEKSNGNTYLNWYLQRPGQSPQLLIYRVSRRYSGVPDRFSGSGSGTDFTLKISRVEAEDVGVYYCLQVTHVPYTFGQGTRLEIK

SEQ ID NO: 30
DAVMTQSPLSLPVTLGQPASISCRSSQSLEKSNGNTYLNWYLQRPGQSPQLLIYRVSRRYSGVPDRFSGSGSGTDFTLKISRVEAEDVGVYFCLQVTHVPYTFGQGTRLEIK

SEQ ID NO: 31
DAVMTQSPLSLPVTLGDPASISCRSSQSLEKSNGNTYLNWYLQRPGQSPQLLIYRVSRRYSGVLDRFSGSGSGTDFTLKISRVEAEDLGVYFCLQVTHVPYTFGGGTRLEIK

SEQ ID NO: 32
DVVMTQTPLSLSVTPGQPASISCRSTQSIVHSNGKTYLEWYLQKPGQSPKLLIYRVSNRFSGVPDRISGSGSGTDFTLKISRVEAEDVGVYYCFQGSHVPFTFGGGTKVEIK

SEQ ID NO: 33
DVLMTQTPLSLSVTPGQPASISCRSTQSIVHSNGKTYLEWYLQKPGQSPKLLIYRVSNRFSGVPDRISGSGSGTDFTLKISRVEAEDVGVYYCFQGSHVPFTFGGGTKVEIK

SEQ ID NO: 34
DVLMTQTPLSLSVTPGDPASISCRSTQSIVHSNGKTYLEWYLQKPGQSPKLLIYRVSNRFSGVPDRISGSGSGTDFTLKISRVEAEDVGVYYCFQGSHVPFTFGGGTKVEIK

Humanized Heavy Chain Variable Domain

SEQ ID NO: 35
QIQLVQSGAEVKKPGASVKVSCKASGYTFIDYYINWVRQAPGQGLEWMGWIYPGSGNTKYNEKFKDRVTLTVDTSSSTAYMELSSLRSEDTAVYYCVRKGIIYNYGSSDVLAYWGQGTLVTVSS

SEQ ID NO: 36
QIQLVQSGAEVKKPGASVKISCKASGYTFIDYYINWVKQAPGQGLEWMGWIYPGSGNTKYNEKFKDRVTLTVDTSSSTAYMELSSLRSEDTAVYFCVRKGIIYNYGSSDVLAYWGQGTLVTVSS

SEQ ID NO: 37
QIQLVQSGAEVKKPGASVKISCKASGYTFIDYYINWVKQRPGQGLEWIGWIYPGSGNTKYNEKFKDRGTLTVDTSSSTAYMELSSLRSEDTAVYFCVRKGIIYNYGSSDVLAYWGQGTLVTVSS

SEQ ID NO: 38
QIQLQQSGAEVKKPGASVKISCKASGYTFIDYYINWVKQRPGQGLEWIGWIYPGSGNTKYNEKFKDRGTLTVDTSSSTAYMELSSLRSEDTAVYFCVRKGIIYNYGSSDVLAYWGQGTLVTVSS

SEQ ID NO: 39
EVQLVQSGAEVKKPGASVKISCKASGYTFTGYYMNWVRQAPGQSLEWIGDLNPDNGDTNYNQKFVGRVTMTVDTSISTAYMELSRLRSEDTAVYYCARGGKGGFDYWGQGTTLTVSS

SEQ ID NO: 40
EVQLVQSGAEVKKPGASVKISCKASGYTFTGYYMNWMKQAPGQSLEWIGDLNPDNGDTNYNQKFVGRVTMTVDTSISTAYMELSRLRSEDTAVYYCARGGKGGFDYWGQGTTLTVSS

SEQ ID NO: 41
EVQLVQSGAEVKKPGASVKISCKASGYTFTGYYMNWMKQAPGKSLEWIGDLNPDNGDTNYNQKFVGRATLTVDTSISTAYMELSRLRSEDTAVYYCARGGKGGFDYWGQGTTLTVSS

SEQ ID NO: 42
EVQLQQSGAEVKKPGASVKISCKASGYTFTGYYMNWMKQSHGKSLEWIGDLNPDNGDTNYNQKFVGRATLTVDKSISTAYMELSRLRSEDTAVYYCARGGKGGFDYWGQGTTLTVSS

SEQ ID NO: 43
QVQLVQSGAEVKKPGASVKVSCKASGYSLINYWVGWVRQAPGQGLEWMGDVYPGGNYTNNNEKLKGRVTLTADTSTSTAYLELSSLRSEDTAVYYCARKGRGGMDYWGQGTTVTVSS

SEQ ID NO: 44
QVQLVQSGAEVKKPGASVKISCKASGYSLINYWVGWVRQAPGQGLEWIGDVYPGGNYTNNNEKLKGRATLTADTSTSTAYLELSSLRSEDTAVYYCARKGRGGMDYWGQGTTVTVSS

SEQ ID NO: 45
QVQLVQSGAEVKKPGASVKISCKASGYSLINYWVGWVRQAPGHGLEWIGDVYPGGNYTNNNEKLKGRATLTADTSTSTAYLELSSLRSEDTAVYFCARKGRGGMDYWGQGTTVTVSS

```
                                                  SEQ ID NO: 46
QVQLQQSGAEVKKPGASVKVSCKASGYSLINYWVGWVRQAPGHGLEWIG
DVYPGGNYTNNNEKLKGRATLTADTSTSTAYLELSSLRSEDTAVYFCAR
KGRGGMDYWGQGTTVTVSS
```

Humanized Light Chains

```
                                                  SEQ ID NO: 47
DIVMTQSPDSLAVSLGERLTINCKSSQSLLYSSNQKNYLAWYQQKPGQP
PKLLIYWASTRESGVPDRFSGSGSGTDFTLTISSVQAEDVAVYYC**HQYY
SYPLT**FGQGTKLELKRTVAAPSVFIFPPSDEQLKSGTASVVCLLNNFYP
REAKVQWKVDNALQSGNSQESVTEQDSKDSTYSLSSTLTLSKADYEKHK
VYACEVTHQGLSSPVTKSFNRGEC
```

```
                                                  SEQ ID NO: 48
DIVMTQSPDSLAVSLGERLTINCKSSQSLLYSSNQKNYLAWYQQKPGQS
PKLLIYWASTRESGVPDRFSGSGSGTDFTLTISSVQAEDVAVYYC**HQYY
SYPLT**FGQGTKLELKRTVAAPSVFIFPPSDEQLKSGTASVVCLLNNFYP
REAKVQWKVDNALQSGNSQESVTEQDSKDSTYSLSSTLTLSKADYEKHK
VYACEVTHQGLSSPVTKSFNRGEC
```

```
                                                  SEQ ID NO: 49
DIVMTQSPSSLAVSLRERLTINCKSSQSLLYSSNQKNYLAWYQQKPGQS
PKLLIYWASTRESGVPDRFSGSGSGTDFTLTISSVKAEDVAVYYC**HQYY
SYPLT**FGQGTKLELKRTVAAPSVFIFPPSDEQLKSGTASVVCLLNNFYP
REAKVQWKVDNALQSGNSQESVTEQDSKDSTYSLSSTLTLSKADYEKHK
VYACEVTHQGLSSPVTKSFNRGEC
```

```
                                                  SEQ ID NO: 50
DVVMTQSPLSLPVTLGQPASISCRSSQSLEKSNGNTYLNWFQQRPGQSP
QLLIYRVSRRYSGVPDRFSGSGSGTDFTLKISRVEAEDVGVYYC**LQVTH
VPYT**FGQGTRLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC
```

```
                                                  SEQ ID NO: 51
DAVMTQSPLSLPVTLGQPASISCRSSQSLEKSNGNTYLNWYLQRPGQSP
QLLIYRVSRRYSGVPDRFSGSGSGTDFTLKISRVEAEDVGVYYC**LQVTH
VPYT**FGQGTRLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC
```

```
                                                  SEQ ID NO: 52
DAVMTQSPLSLPVTLGQPASISCRSSQSLEKSNGNTYLNWYLQRPGQSP
QLLIYRVSRRYSGVPDRFSGSGSGTDFTLKISRVEAEDVGVYFC**LQVTH
VPYT**FGQGTRLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC
```

```
                                                  SEQ ID NO: 53
DAVMTQSPLSLPVTLGDPASISCRSSQSLEKSNGNTYLNWYLQRPGQSP
QLLIYRVSRRYSGVLDRFSGSGSGTDFTLKISRVEAEDLGVYFC**LQVTH
VPYT**FGGGTRLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC
```

```
                                                  SEQ ID NO: 54
DVVMTQTPLSLSVTPGQPASISCRSTQSIVHSNGKTYLEWYLQKPGQSPK
LLIYRVSNRFSGVPDRISGSGSGTDFTLKISRVEAEDVGVYYC**FQGSHVP
FT**FGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC
```

```
                                                  SEQ ID NO: 55
DVLMTQTPLSLSVTPGQPASISCRSTQSIVHSNGKTYLEWYLQKPGQSPK
LLIYRVSNRFSGVPDRISGSGSGTDFTLKISRVEAEDVGVYYC**FQGSHVP
FT**FGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC
```

```
                                                  SEQ ID NO: 56
DVLMTQTPLSLSVTPGDPASISCRSTQSIVHSNGKTYLEWYLQKPGQSPK
LLIYRVSNRFSGVPDRISGSGSGTDFTLKISRVEAEDVGVYYC**FQGSHVP
FT**FGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC
```

Humanized Heavy Chains

```
                                                  SEQ ID NO: 57
QIQLVQSGAEVKKPGASVKVSCKASGYTFIDYYINWVRQAPGQGLEWMG**W
IYPGSGNTKYNEKFKDRVTLTVDTSSSTAYMELSSLRSEDTAVYYCVRKG
IIYNYGSSDVLAY**WGQGTLVTVSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFN
```

-continued

STFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPPM
LDSDGSFFLYSKLTVDKSRWQQGNVFSCSVMHEALHNHYTQKSLSLSPGK

SEQ ID NO: 58
QIQLVQSGAEVKKPGASVKISCKASGYTFIDYYINWVKQAPGQGLEWMGW
IYPGSGNTKYNEKFKDRVTLTVDTSSSTAYMELSSLRSEDTAVYFCVRKG
IIYNYGSSDVLAYWGQGTLVTVSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFN
STFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPPM
LDSDGSFFLYSKLTVDKSRWQQGNVFSCSVMHEALHNHYTQKSLSLSPGK

SEQ ID NO: 59
QIQLVQSGAEVKKPGASVKISCKASGYTFIDYYINWVKQRPGQGLEWIGW
IYPGSGNTKYNEKFKDRGTLTVDTSSSTAYMELSSLRSEDTAVYFCVRKG
IIYNYGSSDVLAYWGQGTLVTVSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFN
STFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPPM
LDSDGSFFLYSKLTVDKSRWQQGNVFSCSVMHEALHNHYTQKSLSLSPGK

SEQ ID NO: 60
QIQLQQSGAEVKKPGASVKISCKASGYTFIDYYINWVKQRPGQGLEWIGW
IYPGSGNTKYNEKFKDRGTLTVDTSSSTAYMELSSLRSEDTAVYFCVRKG
IIYNYGSSDVLAYWGQGTLVTVSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFN
STFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPPM
LDSDGSFFLYSKLTVDKSRWQQGNVFSCSVMHEALHNHYTQKSLSLSPGK

SEQ ID NO: 61
EVQLVQSGAEVKKPGASVKISCKASGYTFTGYYMNWVRQAPGQSLEWIGD
LNPDNGDTNYNQKFVGRVTMTVDTSISTAYMELSRLSEDTAVYYCARGG
KGGFDYWGQGTTLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 62
EVQLVQSGAEVKKPGASVKISCKASGYTFTGYYMNWMKQAPGQSLEWIGD
LNPDNGDTNYNQKFVGRVTMTVDTSISTAYMELSRLSEDTAVYYCARGG
KGGFDYWGQGTTLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 63
EVQLVQSGAEVKKPGASVKISCKASGYTFTGYYMNWMKQAPGKSLEWIGD
LNPDNGDTNYNQKFVGRATLTVDTSISTAYMELSRLSEDTAVYYCARGG
KGGFDYWGQGTTLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 64
EVQLQQSGAEVKKPGASVKISCKASGYTFTGYYMNWMKQSHGKSLEWIGD
LNPDNGDTNYNQKFVGRATLTVDKSISTAYMELSRLSEDTAVYYCARGG
KGGFDYWGQGTTLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 65
QVQLVQSGAEVKKPGASVKVSCKASGYSLINYWVGWVRQAPGQGLEWMGD
VYPGGNYTNNNEKLKGRVTLTADTSTSTAYLELSSLRSEDTAVYYCARKG

RGGMDYWGQGTTVTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 66
QVQLVQSGAEVKKPGASVKISCKASGYSLINYWVGWVRQAPGQGLEWIGD
VYPGGNYTNNNEKLKGRATLTADTSTSTAYLELSSLRSEDTAVYYCARKG
RGGMDYWGQGTTVTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 67
QVQLVQSGAEVKKPGASVKISCKASGYSLINYWVGWVRQAPGHGLEWIGD
VYPGGNYTNNNEKLKGRATLTADTSTSTAYLELSSLRSEDTAVYFCARKG
RGGMDYWGQGTTVTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

SEQ ID NO: 68
QVQLQQSGAEVKKPGASVKVSCKASGYSLINYWVGWVRQAPGHGLEWIGD
VYPGGNYTNNNEKLKGRATLTADTSTSTAYLELSSLRSEDTAVYFCARKG
RGGMDYWGQGTTVTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

---

We claim:

1. An isolated monoclonal anti-CD47 antibody, or an antigen-binding portion thereof, comprising:
   a heavy chain variable region CDR1 comprising SEQ ID NO:16;
   a heavy chain variable region CDR2 comprising SEQ ID NO:19;
   a heavy chain variable region CDR3 comprising SEQ ID NO:22;
   a light chain variable region CDR1 comprising SEQ ID NO:7;
   a light chain variable region CDR2 comprising SEQ ID NO:10; and
   a light chain variable region CDR3 comprising SEQ ID NO:13.

2. The monoclonal antibody, or antigen-binding portion thereof, of claim 1, wherein a light chain variable region amino acid sequence has at least 95% identity to SEQ ID NO:1 and a heavy chain variable region amino acid sequence has at least 95% identity to SEQ ID NO:4.

3. The monoclonal antibody, or an antigen-binding portion thereof, of claim 1, wherein a heavy chain variable region comprising an amino acid sequence that has at least 95%, at least 96%, at least 97%, at least 98%, or at least 99% identical to a sequence as set forth in SEQ ID NO:4.

4. The monoclonal antibody, or antigen-binding portion thereof, of claim 1, which is a Fab fragment, an F(ab')2 fragment, an Fv fragment, a single chain antibody, or a bispecific antibody.

5. The monoclonal antibody of claim 1, which is a chimeric antibody or humanized antibody.

6. The monoclonal antibody of claim 1, which is an immunoglobulin G (IgG), an IgM, an IgE, an IgA or an IgD molecule.

7. An immunoconjugate comprising the antibody, or antigen-binding portion thereof, of claim 1, linked to a therapeutic agent.

8. A pharmaceutical composition comprising the antibody, or antigen-binding portion thereof, according to claim 1 and a pharmaceutically acceptable carrier.

9. A method of stimulating an immune response in a subject, comprising the step of administering to the subject the pharmaceutical composition according to claim 8 in therapeutically effective amount to stimulate an immune response in said subject.

10. A method of treating cancer in a subject, comprising the step of administering to the subject the pharmaceutical composition according to claim 8 in therapeutically effective amount to treat said cancer.

11. A monoclonal antibody or antigen-binding portion thereof, comprising: a heavy chain variable region comprising an amino acid sequence selected from the group consisting of SEQ ID NOs: 35-38 and a light chain variable region comprising an amino acid sequence selected from the group consisting of SEQ ID NOs: 25-27.

12. An isolated monoclonal antibody or antigen binding portion thereof, comprising a light chain comprising an amino acid sequence selected from the group consisting of SEQ ID NOs: 47-53 and a heavy chain comprising an amino acid sequence selected from the group consisting of SEQ ID NOs: 57-64.

13. An isolated monoclonal anti-CD47 antibody, or an antigen-binding portion thereof, comprising:
 a heavy chain variable region CDR1 comprising SEQ ID NO:17;
 a heavy chain variable region CDR2 comprising SEQ ID NO:20;
 a heavy chain variable region CDR3 comprising SEQ ID NO:23;
 a light chain variable region CDR1 comprising SEQ ID NO:8;
 a light chain variable region CDR2 comprising SEQ ID NO:11; and
 a light chain variable region CDR3 comprising SEQ ID NO:14.

14. The monoclonal antibody, or antigen-binding portion thereof, of claim 13, wherein a light chain variable region amino acid sequence has at least 95% identity to SEQ ID NO:2 and a heavy chain variable region amino acid sequence has at least 95% identity to SEQ ID NO:5.

15. The monoclonal antibody, or an antigen-binding portion thereof, of claim 13, wherein a heavy chain variable region comprising an amino acid sequence that has at least 95%, at least 96%, at least 97%, at least 98%, or at least 99% identical to a sequence as set forth in SEQ ID NO:5.

16. The monoclonal antibody, or antigen-binding portion thereof, of claim 13, which is a Fab fragment, an F(ab')$_2$ fragment, an Fv fragment, a single chain antibody, or a bispecific antibody.

17. The monoclonal antibody of claim 13, which is a chimeric antibody or humanized antibody.

18. The monoclonal antibody of claim 13, which is an immunoglobulin G (IgG), an IgM, an IgE, an IgA or an IgD molecule.

19. An immunoconjugate comprising the antibody, or antigen-binding portion thereof, of claim 13, linked to a therapeutic agent.

20. A pharmaceutical composition comprising the antibody, or antigen-binding portion thereof, according to claim 13 and a pharmaceutically acceptable carrier.

21. A method of stimulating an immune response in a subject, comprising the step of administering to the subject the pharmaceutical composition according to claim 20 in therapeutically effective amount to stimulate an immune response in said subject.

22. A method of treating cancer in a subject, comprising the step of administering to the subject the pharmaceutical composition according to claim 20 in therapeutically effective amount to treat said cancer.

23. A monoclonal antibody, or antigen-binding portion thereof, comprising: a heavy chain variable region comprising an amino acid sequence selected from the group consisting of SEQ ID NOs: 39-42 and a light chain variable region comprising an amino acid sequence selected from the group consisting of SEQ ID NOs: 28-31.

* * * * *